(12) United States Patent
Smith et al.

(10) Patent No.: US 9,770,258 B2
(45) Date of Patent: Sep. 26, 2017

(54) ATHERECTOMY DEVICES

(71) Applicant: AtheroMed, Inc., Menlo Park, CA (US)

(72) Inventors: Torrey Smith, Redwood City, CA (US); Paul Quentin Escudero, Redwood City, CA (US); Douglas E. Rowe, San Jose, CA (US); August Christopher Pombo, Sacramento, CA (US)

(73) Assignee: ATHEROMED, INC., Menlo Park, CA (US)

( * ) Notice: Subject to any disclaimer, the term of this patent is extended or adjusted under 35 U.S.C. 154(b) by 360 days.

(21) Appl. No.: 14/329,805

(22) Filed: Jul. 11, 2014

(65) Prior Publication Data

US 2015/0150587 A1 Jun. 4, 2015

Related U.S. Application Data

(60) Provisional application No. 61/860,843, filed on Jul. 31, 2013, provisional application No. 61/937,440, filed on Feb. 7, 2014.

(51) Int. Cl.
*A61B 17/22* (2006.01)
*A61B 17/3207* (2006.01)
*A61B 17/32* (2006.01)
*A61M 25/00* (2006.01)
*A61B 17/00* (2006.01)

(52) U.S. Cl.
CPC ............ *A61B 17/320758* (2013.01); *A61B 17/32002* (2013.01); *A61B 2017/003* (2013.01); *A61B 2017/00309* (2013.01); *A61B 2017/00331* (2013.01); *A61B 2017/00469* (2013.01); *A61B 2017/00685* (2013.01); *A61B 2017/00778* (2013.01); *A61B 2017/22001* (2013.01); *A61B 2017/22038* (2013.01); *A61B 2017/22041* (2013.01); *A61B 2017/320766* (2013.01);
(Continued)

(58) Field of Classification Search
CPC ...... A61B 17/320758; A61B 17/32002; A61B 17/22; A61B 2017/320775
See application file for complete search history.

(56) References Cited

U.S. PATENT DOCUMENTS 5,114,399 A  5/1992 Kovalcheck
5,304,189 A  4/1994 Goldberg et al.
(Continued)

FOREIGN PATENT DOCUMENTS

EP    2 462 881 A1    6/2012
WO    2013/056262 A1    4/2013
WO    2015/017114 A2    2/2015

OTHER PUBLICATIONS

International Search Report and Written Opinion, mailed Feb. 10, 2015, for International Application PCT/US14/46432, filed Jul. 11, 2014 (10 pages).

*Primary Examiner* — Ashley Fishback

(57) ABSTRACT

Described here are devices and components for use in performing an atherectomy. Generally, the atherectomy devices may have a handle, a cutter assembly, and a catheter or catheter assembly therebetween. The cutter assembly may include a housing and a cutter comprising a proximal cutter and a distal cutter, each of which may be rotated relative to the atherectomy device to cut occlusive material.

8 Claims, 16 Drawing Sheets

(52) U.S. Cl.
CPC .............. *A61B 2017/320775* (2013.01); *A61B 2217/007* (2013.01); *A61M 25/0054* (2013.01)

(56) References Cited

U.S. PATENT DOCUMENTS

| | | |
|---|---|---|
| 6,258,109 B1 | 7/2001 | Barry |
| 6,497,711 B1 | 12/2002 | Plaia et al. |
| 6,565,588 B1 | 5/2003 | Clement et al. |
| 6,620,148 B1 | 9/2003 | Tsugita |
| 2002/0107479 A1* | 8/2002 | Bates ............... A61B 17/22031 604/96.01 |
| 2009/0018566 A1 | 1/2009 | Escudero et al. |
| 2013/0096587 A1 | 4/2013 | Smith et al. |

* cited by examiner

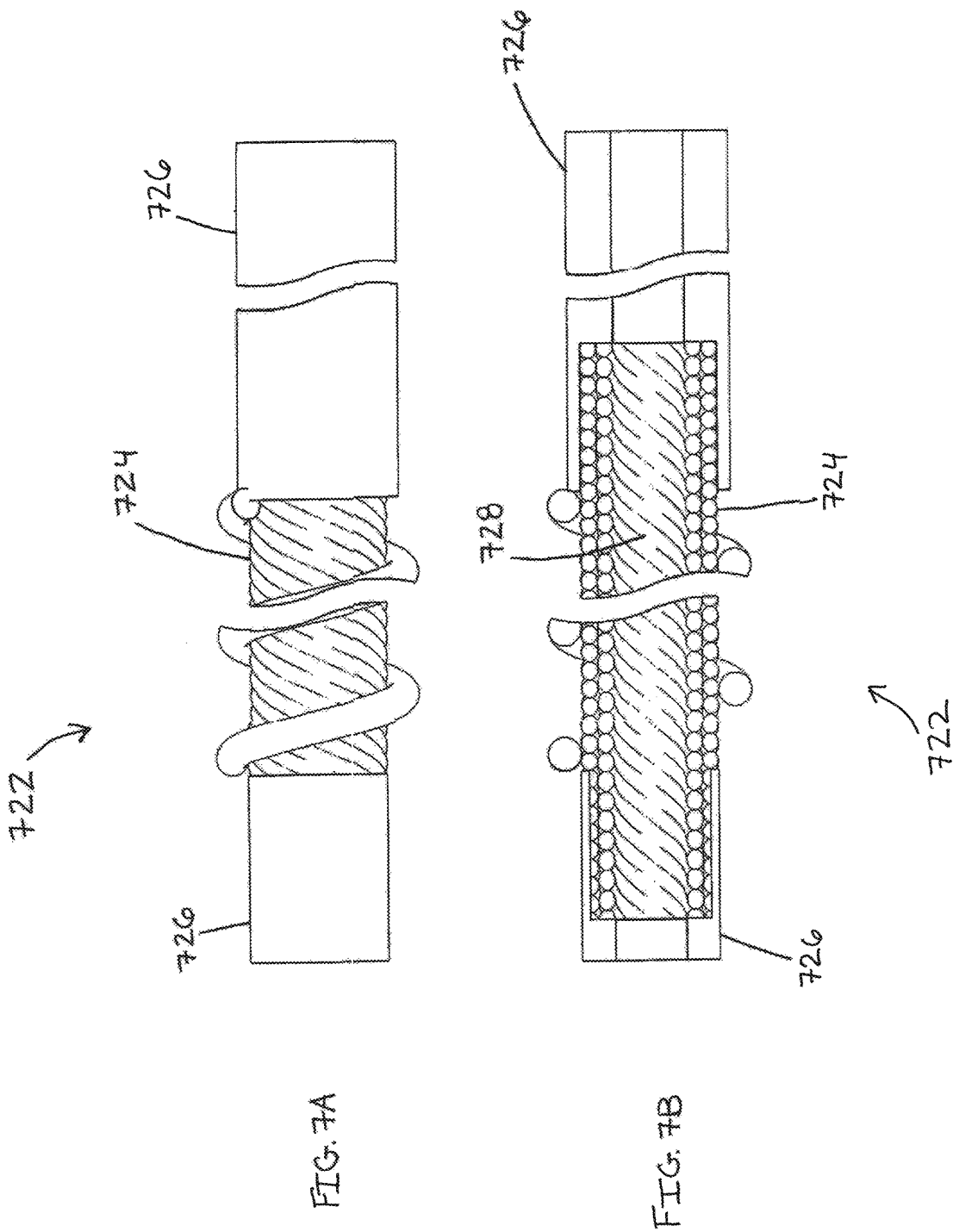

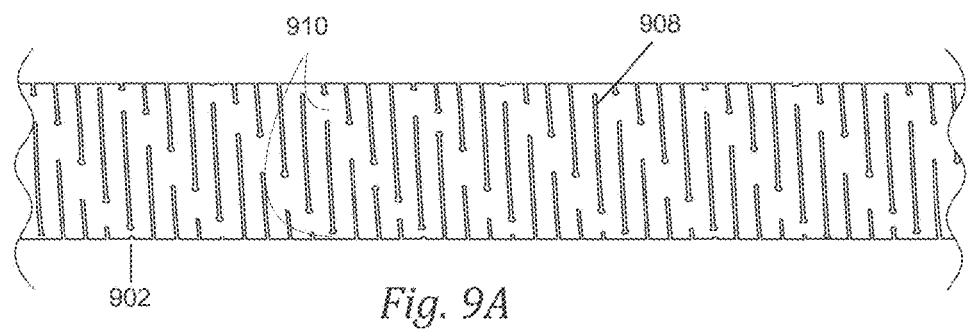
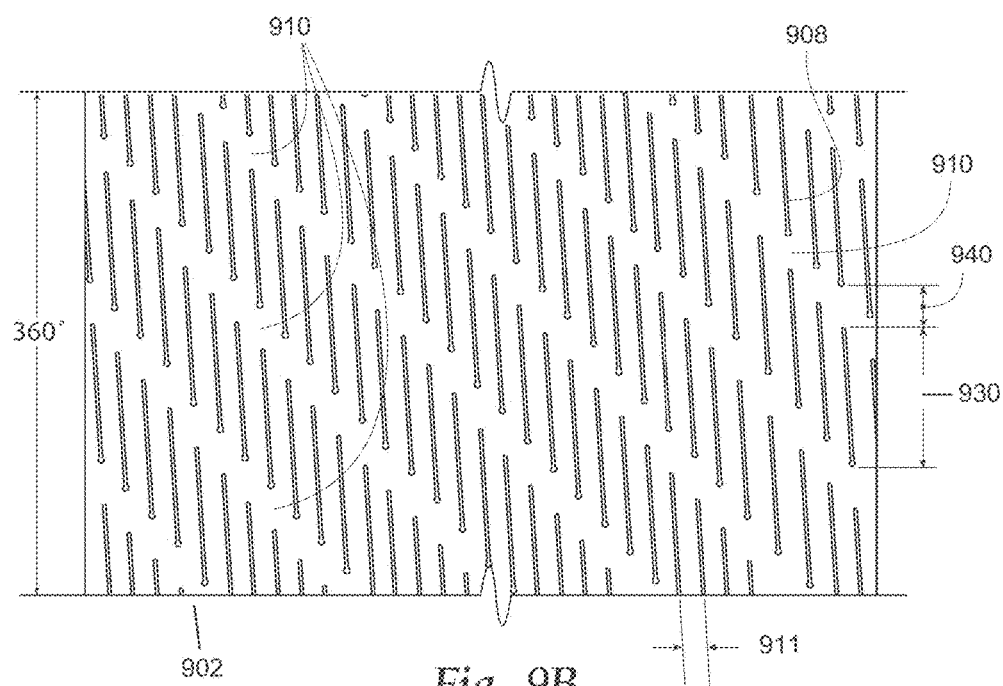
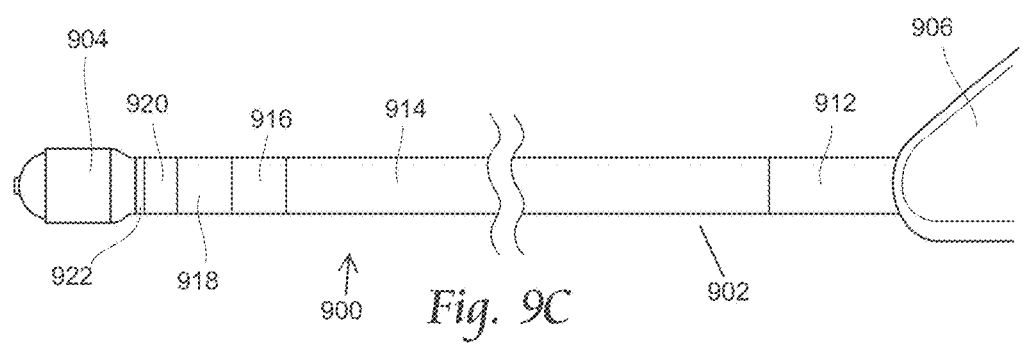

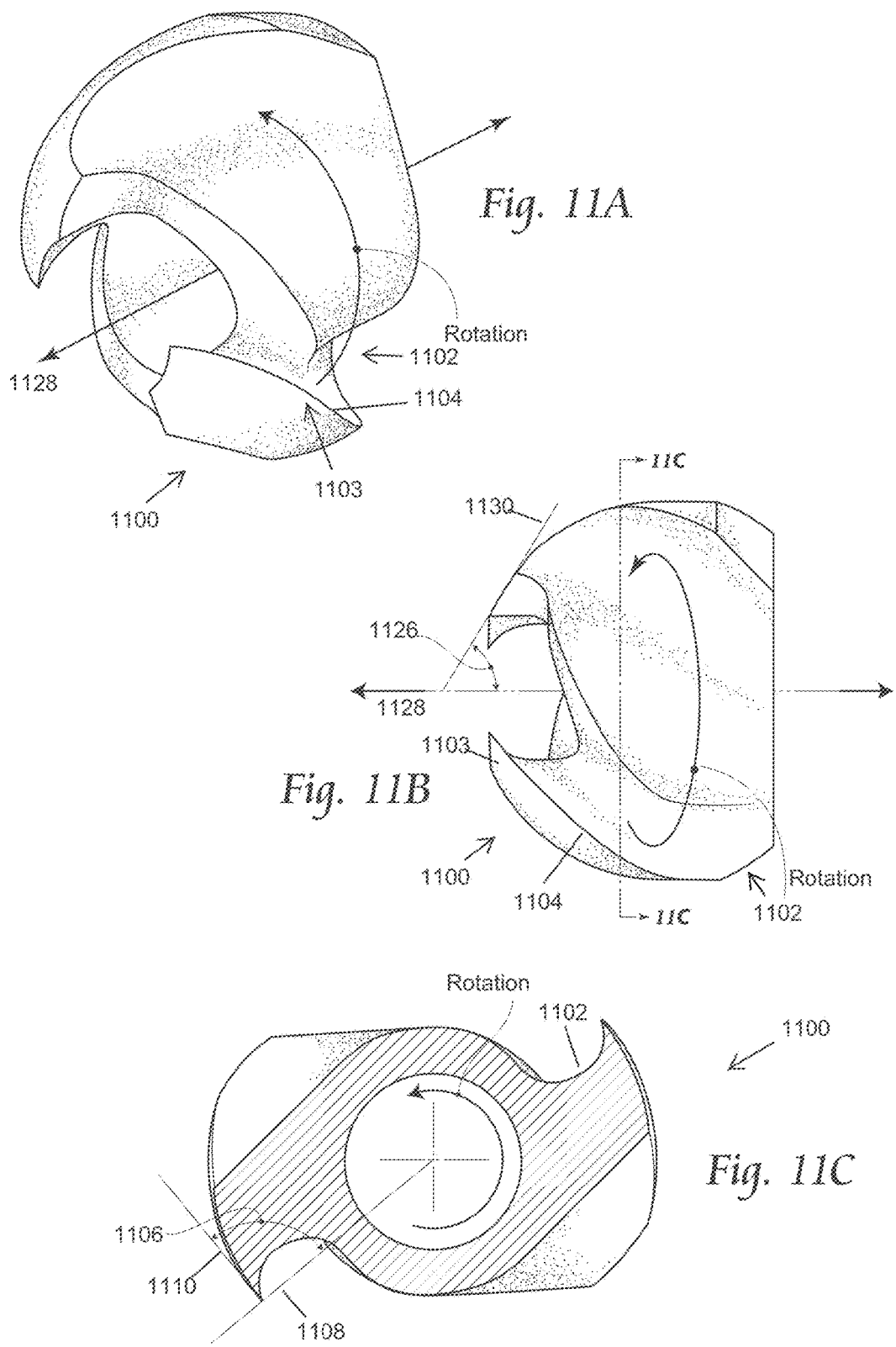

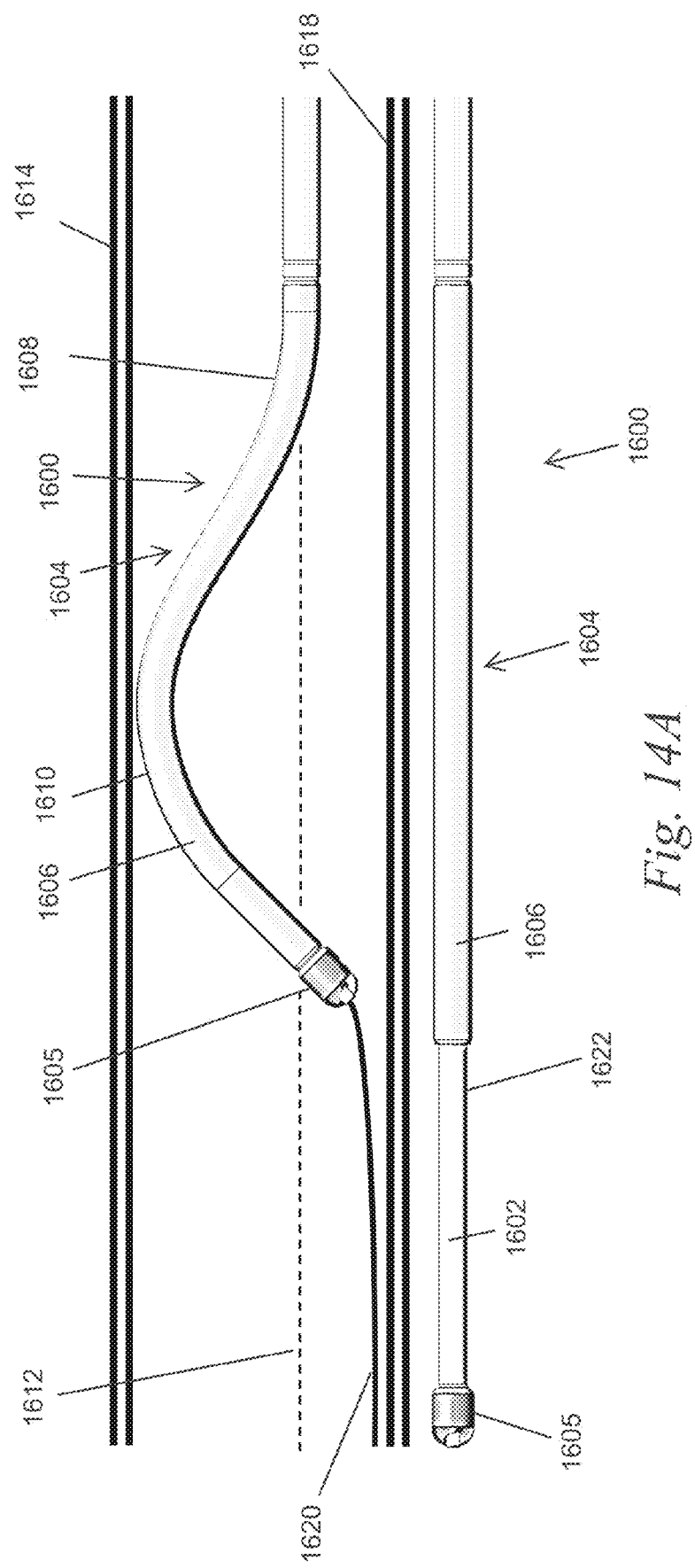

ATHERECTOMY DEVICES

CROSS-REFERENCE TO RELATED APPLICATIONS

This application claims priority to U.S. Provisional Application Ser. No. 61/937,440, filed on Feb. 7, 2014, entitled "ATHERECTOMY DEVICES," and to U.S. Provisional Application Ser. No. 61/860,843, filed on Jul. 31, 2013, entitled "ATHERECTOMY DEVICES," the content of each of which is hereby incorporated in its entirety.

FIELD

The devices and methods described herein generally relate to treatment of occluded body lumens, such as the removal of occlusive material from a blood vessel or other body parts.

BACKGROUND

Coronary artery disease and peripheral vascular disease can arise due to the narrowing of the arteries by atherosclerosis (also called arteriosclerosis). Coronary artery disease generally affects arteries of the heart—arteries that carry blood to cardiac muscles and surrounding tissue. Peripheral vascular disease refers to various diseases of the vascular system outside the heart and brain, which carries blood, for example, to the legs.

Atherosclerosis commonly affects the medium and large arteries, and may occur when fat, cholesterol, and other substances build up on the walls of arteries and form fleshy or hard/calcified structures called plaques/lesions. As plaque forms within the native arterial wall, the artery may narrow and become less flexible, which may make it more difficult for blood to flow therethrough. In the peripheral arteries, the plaque is typically not localized, but can extend in length along the axis of the artery for as much as 10 mm or more (in some instance up to 400 mm or more).

A number of interventional surgical methodologies may be used to treat atherosclerosis. In balloon angioplasty, for example, a physician may advance a collapsed, intravascular balloon catheter into a narrowed artery, and may inflate the balloon to macerate and/or displace plaque against the vessel wall. A successful angioplasty may help reopen the artery and allow for improved blood flow. Often, balloon angioplasty is performed in conjunction with the placement of a stent or scaffold structure within the artery to help minimize re-narrowing of the artery. Balloon angioplasty, however, can stretch the artery and induce scar tissue formation, while the placement of a stent can cut arterial tissue and also induce scar tissue formation. Scar tissue formation may lead to restenosis of the artery. In some instances, balloon angioplasty can also rip the vessel wall.

Atherectomy is another treatment methodology for atherosclerosis, and involves the use of an intravascular device to mechanically remove (e.g., debulk) plaque from the wall of the artery. Atherectomy devices may allow for the removal of plaque from the wall of an artery, reducing the risk of stretching, cutting, or dissecting the arterial wall and causing tissue damage that leads to restenosis. In some instances, atherectomy may be used to treat restenosis by removing scar tissue.

Current atherectomy treatments suffer from structural and performance limitations. For example, currently-available atherectomy devices with rotating burrs generally are not configured to capture particles that are released as the burr grinds/sands tissue, which may result in diminished downstream blood flow resulting from particle residue. Additionally, these rotating burrs may cause hemolysis, and are generally limited as an adjunct therapy to angioplasty. Other systems may include expandable cutters with foldable/movable cutting wings and vacuum-driven aspiration supplied via a vacuum pump, which may cause the artery to collapse on to the cutter and perforate the arterial wall. Other atherectomy systems may include a side-window eccentric cutter and distal nosecone which receives material from the cutter. Because the nosecone can only hold a limited volume of plaque, a surgeon may need to repeatedly withdraw the cutter and flush plaque and other material from the nosecone. It is therefore desirable to provide improved atherectomy devices and methods.

BRIEF SUMMARY

Described here are devices, systems, and methods for removing occlusive material from one or more vessels. Generally, the devices may comprise a catheter and a cutter assembly coupled to a distal end of the catheter. In some of these variations, the cutter assembly may comprise a cutter comprising helical flutes, a guide wire lumen, and a port. In some of these variations, the port may comprise an opening extending from the guide wire lumen to an outside surface of the cutter. In some of these variations, the cutter may comprise a proximal cutter and a distal cutter. In some of these variations, the proximal cutter may comprise a stem configured to fit within a central lumen of the distal cutter, and the port may be located on the stem of the proximal cutter. In some of these variations, the port may have a cross-sectional area of less than 50% of the cross-sectional area of the stem. In some variations, a first portion of the stem of the proximal cutter may be covered by the distal cutter, and a second portion of the stem of the proximal cutter may be exposed by the distal cutter. In some of these variations, the port may be exposed by the distal cutter. In some variations, a first portion of the stem of the proximal cutter may be covered by the distal cutter, and a second portion of the stem of the proximal cutter may be exposed by the distal cutter. In some of these variations, the port may be covered by the distal cutter, and the device may further comprise a second port in the distal cutter. In some of these variations, the port on the stem of the proximal cutter and the second port may form a contiguous opening from the central lumen of the cutter assembly through the proximal and distal cutters. In some variations, the port may be angled proximally from the central lumen to the outside surface of the cutter. In some variations, the cross-sectional area of the port may increase from the central lumen to the outside surface of the cutter.

In some variations, the devices may comprise a catheter, a torque shaft within the catheter comprising a coiled shaft, and a cutter assembly. In some of these variations, a distal end of the torque shaft may be attached to a proximal end of the cutter assembly via an end cap attached to a distal end of the coiled shaft. In some of these variations, the cutter assembly may comprise a cutter and a housing, and the housing may have an inner diameter of less than or equal to 0.06 inches. In some of these variations, the percentage of the cross-sectional area within the inner diameter of the housing available for cutting and conveying occlusive material may be greater than or equal to 65%. In some variations, the cutter assembly may comprise a cutter and a housing, and the housing may have an inner diameter of less than or equal to 0.077 inches. In some of these variations, the percentage of the cross-sectional area within the inner diameter of the housing available for cutting and conveying occlusive material may be greater than or equal to 78%. In some variations, the cutter assembly may comprise a cutter and a housing, and the housing may have an inner diameter of less than or equal to 0.084 inches. In some of these variations, the percentage of the cross-sectional area within the inner diameter of the housing available for cutting and conveying occlusive material may be greater than or equal to 80%. In some variations, the proximal end of the cutter assembly may be attached to a distal end of the end cap. In some variations, the cutter assembly may not comprise a counterbore for attaching the torque shaft to the cutter assembly. In some variations, the distal end of the coiled shaft may have been centerless ground.

In some variations, the systems may comprise a device comprising catheter, a handle coupled to a proximal end of the catheter, and a cutter assembly coupled to a distal end of the catheter, and a guide wire. In some of these variations, the handle may comprise a clip configured to hold a portion of the guide wire fixed relative to the handle. In some of these variations, the clip may comprise a first end configured to releasably connect to the handle and a second end configured to releasably connect to the guide wire. In some of these variations, the guide wire may form a first portion extending proximally from the handle, a second portion extending distally from the clip, and a support loop located between the first and second portions having an arched shape. In some of these variations, the support loop may have a radius of curvature between 3 cm and 8 cm. In some of these variations, the device may be configured to track freely over the guide wire.

BRIEF DESCRIPTION OF THE DRAWINGS

FIGS. 7A and 7B depict cross-sectional and side views, respectively, of a representative torque shaft as described here.

FIG. 9A is a side view of a portion of a variation of a catheter body suitable for use with the atherectomy systems described here. FIG. 9B depicts a plane view of the portion of the catheter body shown in FIG. 9A opened up into a sheet configuration. FIG. 9C depicts a side view of an atherectomy apparatus including the catheter body shown in FIGS. 9A and 9B.

FIGS. 11A and 11B depict a perspective distal view and a side view, respectively, of a variation of a representative cutting element as described here. FIG. 11C is a cross-sectional view of the representative cutting element taken along line 11C-11C in FIG. 11B.

FIGS. 14A and 14B depict a variation of the atherectomy apparatuses described here.

DETAILED DESCRIPTION

Described herein are devices and components for use in performing an atherectomy. Specifically, the various elements described here may be configured to be incorporated into any of the atherectomy devices described in U.S. patent application Ser. No. 13/652,352, filed Oct. 15, 2012, and titled "Atherectomy Apparatus, Systems and Methods," the content of which is hereby incorporated by reference its entirety. Generally, the atherectomy device may comprise a handle, a cutter assembly, and at least one catheter connecting the handle and the cutter assembly. The atherectomy device may include a torque shaft, which may extend through the catheter, and which may be configured to rotate a cutter relative to the catheter. In some instances, the torque shaft may include a conveyor member configured to move cut occlusive material along the torque shaft.

Figure 1:
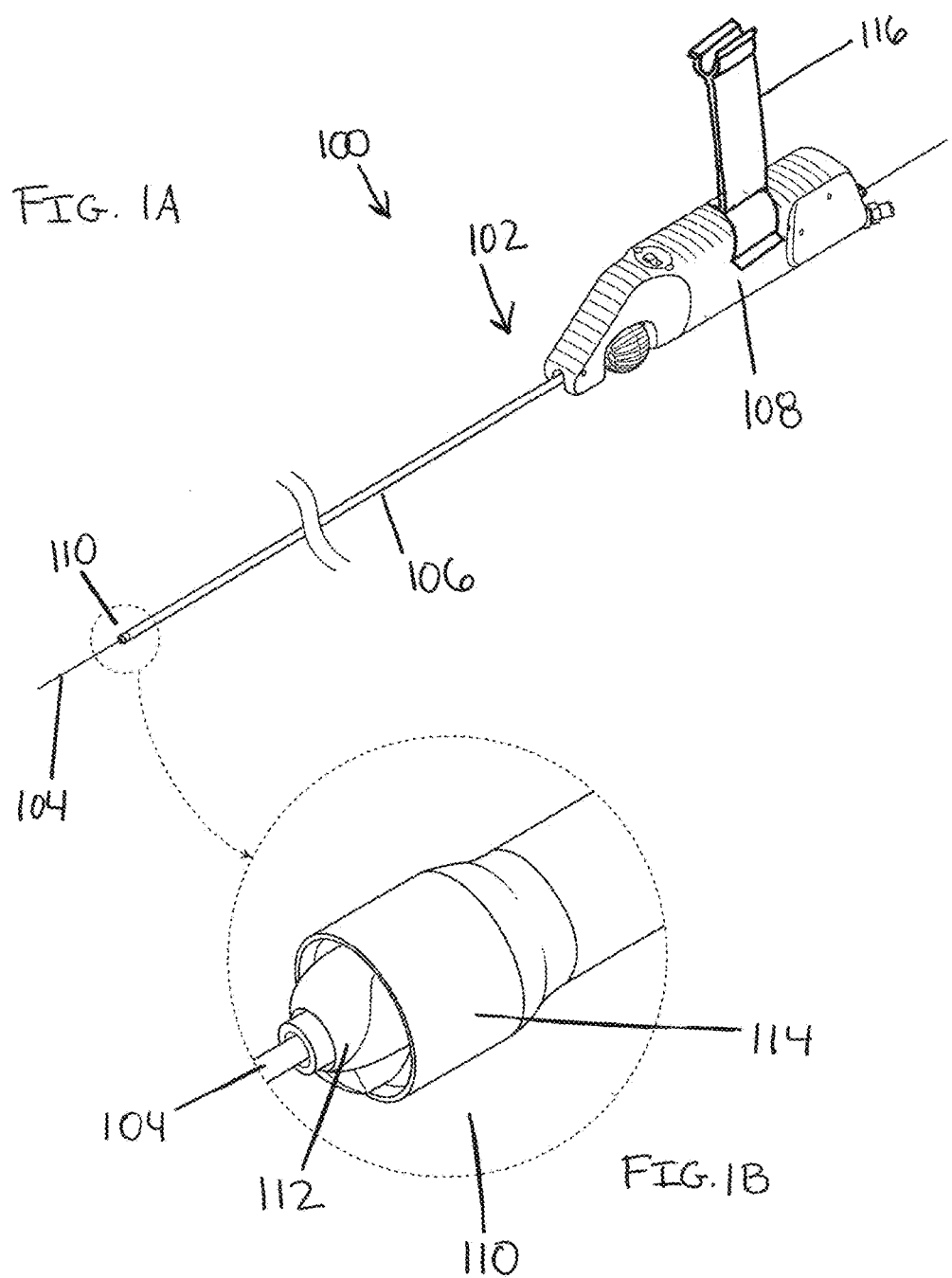
FIG. 1A depicts a perspective view of an illustrative variation of an atherectomy system as described here.
FIG. 1B shows an enlarged perspective view of a distal portion of the atherectomy system shown in FIG. 1A.

FIGS. 1A and 1B show a representative embodiment of the atherectomy systems described here. As shown there, the atherectomy system 100 may include an intravascular atherectomy apparatus 102 and a guide wire 104 over which the atherectomy apparatus 102 may be deployed. While shown in FIGS. 1A and 1B as being advanced over a guide wire, it should be appreciated that in some variations the atherectomy apparatus 102 may be advanced without a guide wire, and in other variations the atherectomy apparatus 102 may comprise a guide wire attached to a distal portion of the atherectomy apparatus 102. The atherectomy apparatus 102 generally includes an elongated catheter 106 having a central axis. The catheter 106 may be sized and configured to be advanced in a blood vessel (e.g., over the guide wire 104) from an external percutaneous access site. The atherectomy apparatus 102 may also include a handle 108, which may be coupled to the proximal (i.e., closest to the user) end of the catheter 106. The handle 108 may be sized and configured to be held and manipulated by a user outside the patient's body. In some variations, the atherectomy device may optionally comprise a support clip 116 configured to releasably hold a portion of the guide wire 104 relative to the handle 108, as will be described in more detail below. The atherectomy apparatus 102 may further comprise a cutter assembly 110 at the distal end of the catheter 106. Generally, the cutter assembly 110 may act to cut and capture occlusive material, and thereby remove the occlusive material from the vessel, which may open the vessel to blood flow. In some variations, the cutter assembly 110 may comprise a rotatable cutter 112, which may be at least partially housed within a housing 114. In the variation shown in FIGS. 1A and 1B, the housing 114 may be open at its distal-most end such that the distal-most end of the cutter may project a distance distally from the housing 114. In some of these variations, when the cutter assembly 110 is deployed in the targeted region where the occlusive materials exist, there may be no structure or component of the atherectomy located in front of (i.e., distal to) the cutter assembly, and thus the first region of the atherectomy apparatus to interact with the plaque is the cutter assembly. It should be appreciated that the atherectomy apparatus 102 may comprise any suitable cutter assembly, such as those described in more detail below.

The Catheter Body

Dimensions

For practical purposes, the outer diameter of any section of the catheter body, including the cutter assembly it carries, may be based at least partially by the anatomy of the intravascular path and the intended target region. Specifically, it may be desirable to increase or maximize the cutting effectiveness of the cutter assembly by maximizing the diameter of the cutter, while minimizing the potential of puncture or trauma to the vessel. Additionally, the outer diameter of the catheter body/cutter assembly may also result at least partially from the diameter of a guide sheath or introducer selected that may be placed at an access site to allow introduction of the atherectomy apparatus into the vasculature. It may be desirable to select a guide sheath or introducer sized to minimize pain, trauma, and blood loss during use, and to facilitate rapid closure of the access incision after removal, to thereby reduce the incidence of interventional complications.

Diameters of the peripheral arteries of the leg vary typically from relatively small in regions below the knee (2.0 mm) to relatively large in regions above the knee (7.0 mm). For percutaneous access to the peripheral arteries (diagnostic and/or interventional purposes), clinicians typically use guide sheaths sized from 5F to 7F, but other sizes may also be used.

Assuming, for example, that a 7F guide sheath would likely be, from a clinical perspective, the largest selected to access the larger vessels above the knee (4 mm to 7 mm), and allowing for a reasonable clearance tolerance between the catheter body/cutter assembly and the guide sheath, in some instances the outer diameter of the catheter body for introduction through such a guide sheath may be selected to be approximately equal to or less than about 2.4 mm. Assuming that a 5F guide sheath would likely be, from a clinical perspective, the largest used to access the smaller vessels below the knee (2.5 mm to 3 mm), and allowing for a reasonable clearance tolerance between the catheter body/cutter assembly and the guide sheath, in some instances the outer diameter of the catheter body for introduction through such a guide sheath may be selected to be approximately equal to or less than about 1.8 mm. In other instances, a 4F guide sheath may be used, and in some of these instances the outer diameter of the catheter body for introduction through such a guide sheath may be selected to be approximately equal to or less than about 1.0 mm. This may in some cases allow for an access site near the foot. Assuming that an intermediate 6 French guide sheath would likely be, from a clinical perspective, the largest used to access the intermediate vessels near the knee (3 mm to 4 mm), and allowing for a reasonable clearance tolerance between the catheter body/cutter assembly and the guide sheath, in some instances the outer diameter of the catheter body for introduction through such a guide sheath may be selected to be approximately equal to or less than about 2.2 mm.

In some examples, that the outer diameter of the cutter assembly may be maximized, to maximize the overall cutting area of the atherectomy assembly. When the cutter assembly of an atherectomy apparatus is the distal-most component of the apparatus, the cutter assembly may lead the way by cutting through the occlusive materials. With regard to the catheter body, however, there may functional and clinical benefits that arise when the outer diameter of the catheter body is not maximized to match the outer diameter of the cutter assembly. Reducing the diameter of the catheter body relative to the cutter assembly may minimize frictional contact between the catheter body and the vessel wall. This may lessen the force required to advance the catheter body through the vasculature and occlusive material, and may help prevent the catheter body from dragging against or sticking to tissue structures in the vessel, or otherwise impeding the progress of the cutter assembly through the occlusive materials.

For example, the outer diameter of the catheter body proximal of the cutter assembly may be sized smaller than the outer diameter of the cutter assembly. In other instances, it may be desirable that the outer diameter of the catheter body proximal of the cutter assembly be sized equal to or smaller than the outer diameter of the cutter assembly.

The reduced diameter of the catheter body may also permit the injection of radiographic contrast material around the catheter body in the guide sheath. For example, an atherectomy apparatus for introduction through a 7F introducer system may have a 2.4 mm diameter cutter assembly and a catheter body having a 2.2 mm diameter. In other variations, however, an atherectomy apparatus for introduction through a 7F introducer system may have a cutter assembly with a diameter between about 1.8 mm and about 2.5 mm, and a catheter body having a diameter between about 1.8 mm and about 2.5 mm. As another example, an atherectomy apparatus for introduction through a 5F or 6F introducer system may have a 1.8 mm diameter cutter assembly and a catheter body having a 1.6 mm diameter, or a 2.2 mm diameter cutter assembly and a catheter body having a 1.6 mm diameter. In other variations, however, an atherectomy apparatus for introduction through a 5F or 6F introducer system may have a cutter assembly with a diameter between about 1.2 mm and about 1.9 mm and a catheter body having a diameter between about 1.2 mm and about 1.9 mm, or a cutter assembly with a diameter between about 1.2 mm and about 2.3 mm and a catheter body having a diameter between about 1.2 mm and about 2.3 mm. As yet another example, an atherectomy apparatus for introduction through a 4F introducer system may have a 1.0 mm diameter cutter assembly and a catheter body having a 0.9 mm diameter. In other variations, however, an atherectomy apparatus for introduction through a 4F introducer system may have cutter assembly with a diameter between about 0.5 mm and about 1.1 mm, and a catheter body having a diameter between about 0.5 mm and about 1.1 mm.

Catheter Properties

In addition to the anatomical and clinical considerations that may be used in selecting an outer diameter of a catheter body, the catheter body may also desirably possess certain physical and mechanical properties, such as those described immediately below, which may enhance the function of the catheter body to support and guide passage of the cutter assembly through the intravascular path and the occlusive materials.

Column Stiffness (Pushability)

One potentially desirable property for the catheter body includes column stiffness. Expressed in units of inch/foot-pounds, column stiffness is the capability of the catheter body to withstand an axial load or compression while resisting bending. Column stiffness can be measured and characterized in conventional ways, and may be referred to as "pushability" herein. Generally, a higher column stiffness is desirable, and may allow the catheter body to transmit a higher axial force (compression) applied at the handle to the cutter assembly without buckling. Accordingly, in some examples, the catheter body may possess column stiffness sufficient to push the cutter assembly over the guide wire without buckling. A column stiffness of 0.050 inches/lbf or greater may be desirable for the catheter bodies described here.

Tensile Stiffness (Pullability)

Another potentially desirable property for the catheter body comprises tensile stiffness. Expressed in units of inch/foot-pounds, tensile stiffness is the capability of the catheter body of withstanding tension while being stretched or pulled before the cross section starts to significantly contract (called "necking"). Tensile stiffness can be measured and characterized in conventional ways, and may be referred to as "pullability" herein. Generally, a high tensile stiffness may be desirable, and may allow the catheter body to be pulled proximally along an intravascular path (e.g., to withdraw the cutter assembly) without necking. A tensile stiffness of 0.050 inches/lbf or greater may be desirable for the catheter bodies described here.

Torsional Stiffness (Torquability)

Another potentially desirable property for the catheter body comprises torsional stiffness. Expressed in degrees/ounce-inch, torsional stiffness is the capability of the catheter body to transmit a rotational load (torque) without untwisting, over-twisting and/or deforming. Torsional stiffness may be measured and characterized in conventional ways, and may be referred to as "torquability" herein. The torsional stiffness may control the capability of the catheter body to transmit a given amount of rotation applied at its proximal end (i.e., the handle) to achieve a comparable amount of rotation at its distal end (i.e, the cutter assembly). A higher torsional stiffness may be desirable, to better allow for rotational transmission along the atherectomy apparatus (i.e., around a guide wire), without twisting or deforming. A torsional stiffness that achieves a 1:1 relationship between rotation applied at the proximal end and the rotation observed at the distal end may be desirable for the catheter bodies described here.

Bending Stiffness (Trackability)

Another potentially desirable property for the catheter body comprises bending stiffness. Expressed in units of a bend radius (in inches), bending stiffness is the ability of the catheter shaft to bend in response to an applied bending force, without breaking or deforming (i.e., without taking a set). Bending stiffness is an extensive material property that can be measured and characterized in conventional ways, and may be referred to as "trackability" herein. Generally, a lower bending stiffness may be desirable to allow the catheter body to be navigated over a guide wire around sharp bends in the vasculature. A targeted bending stiffness of about 0.5 inches (bend radius) or greater at mid-length of the catheter body may be desirable for the catheter bodies described here. In other variations, a targeted bending stiffness of about 0.1 to about 1 inches (bend radius) at mid-length of the catheter body may be desirable for the catheter bodies described here. In yet other variations, a targeted bending stiffness of about 0.3 to about 0.8 inches (bend radius) at mid-length of the catheter body may be desirable for the catheter bodies described here. If the catheter body includes an active deflection component at its distal end (as will be described in greater detail later), a targeted bending stiffness of about 1.0" (bend radius) at the deflectable distal end may be desirable for the catheter bodies described here. In other variations having an active deflection component at its distal end, a targeted bending stiffness of about 0.5 inches to about 2 inches (bend radius) at the deflectable distal end may be desirable for the catheter bodies described here. In other variations having an active deflection component at its distal end, a targeted bending stiffness of about 0.7 inches to about 1.3 inches (bend radius) at the deflectable distal end may be desirable for the catheter bodies described here. A prescribed minimum bend radius also makes it possible to coil the catheter body for packaging without taking a set.

Conventionally, trackability is thought to be inversely related to pushability/pullability and torquability. That is, greater pushability, pullability, and/or torquability in a catheter body may reduce the trackability of the catheter body. However, the catheter bodies described here may balance the pushability, pullability, torquability, and trackability for a given catheter body. The result may be a catheter body that is trackable, yet also possesses the requisite column strength, tensile strength, and torsional stiffness to be sufficiently pushable, pullable and torquable to allow navigation and advancement of a cutter assembly.

The overall trackability of a given catheter body (in terms of its ability to reliably navigate over a guide wire) may be influenced mainly by the physical and mechanical characteristics of the catheter body at its distal end. The pushability, pullability, and torquability may be influenced mainly by the physical and mechanical characteristics of the catheter body proximal to its distal end. That is, the overall configuration of different regions of a catheter body may impart characteristics to the overall length of the catheter body, which may allow for optimization of the overall pushability, pullability, torquability, and trackability of the catheter body.

Generally, the column stiffness, tensile stiffness, torsional stiffness, and bending stiffness for a catheter body may be at least partially determined by its constituent material or materials, the dimensions of catheter body (e.g., the interior diameter, the outer diameter, wall thickness, etc.) and other structural features such as patterning.

FIGS. 6A-6C and 7A-7C depict illustrative variations of the catheter bodies suitable for use with the atherectomy apparatuses described here. In these variations, the catheter bodies may be fabricated from a metal tube (for example, a type 304 stainless steel tube or the like). The dimensions of the tube may depend at least partially on the intended use of the atherectomy apparatus. For example, in some variations the outer diameter of the tube may desirably be about 2.2 mm, while in other variations the outer diameter of the tube may be about 1.6 mm. As another example, in other variations the outer diameter of the tube may desirably be about 1.8 mm to about 2.5 mm, or in other variations the outer diameter of the tube may be about 1.2 to about 1.9 mm. Additionally or alternatively, the wall thickness of the tube may preferably be about 0.288 mm. In other variations, the wall thickness of the tube may preferably be between about 0.1 mm and about 0.5 mm. In other variations, the wall thickness of the tube may preferably be between about 0.2 mm and about 0.4 mm. In yet other variations, the wall thickness of the tube may preferably be between about 0.2 mm and about 0.3 mm. Additionally or alternatively, the overall length of the tube may preferably be about 1437 mm (about 56.56 inches). In other variations, the overall length of the tube may preferably be about 500 mm to about 2500 mm. In other variations, the overall length of the tube may preferably be about 800 mm to about 2200 mm. In other variations, the overall length of the tube may preferably be about 1200 mm to about 1800 mm.

A metal tube with some or all of the dimensions described immediately above may provide a high degree of pushability, pullability, and torquability, the baseline bending stiffness may limit the trackability of the catheter body given the length of the catheter body. Accordingly, in some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

Helical Cut Patterns

In some variations, one or more zones may comprise a helical cut pattern. For example, FIGS. 9A-9C depict a variation of an atherectomy apparatus 900 comprising a catheter body 902, a cutter assembly 904, and a handle 906. Specifically, FIG. 9C shows a side view of the atherectomy apparatus 900, FIG. 9A shows a side view of a section of the catheter body 902, and FIG. 9B depicts a plane view of the section of the catheter body shown in FIG. 9A opened up into a sheet. As shown there, the catheter body 902 may be formed from a tube and may comprise zones of cut patterns in the form of helical cuts 908 (which may be laser cut) that thread around the longitudinal axis of the catheter body 902. The helical cuts 908 are separated by uncut regions call "posts" 910. The direction (thread) of a given pattern can be characterized in terms of its direction about the axis —a left hand thread (when viewed from the proximal end, counterclockwise) or a right hand thread (when viewed from the proximal end, clockwise). The pattern can be further characterized in terms of the arc 930 of the helical cuts 908 about the longitudinal axis (in degrees), and the arc 940 of the uncut region/post between cuts 910 about the longitudinal axis (in degrees). The pattern can be further characterized in terms of the axial separation of the cuts (in inches) along the axis, which can also be called the "pitch" 911.

For example, a cut pattern characterized as "Right Hand Thread, 100° Cut/30° Uncut, 0.012" Pitch" may be used to describe a helical cut pattern that extends clockwise when viewed from the proximal end of the catheter body, in which the helical cuts thread 100 degrees about the longitudinal axis, the posts between helical cuts extend 30 degrees about the axis, and wherein helical cuts are axially separated by 0.012 inches. It should be appreciated, however, that "Right Hand Thread, 100° Cut/30° Uncut, 0.012" Pitch" may be used to describe cut patterns in which the helical cuts may thread between about 90 degrees and about 110 degrees about the longitudinal axis, the posts between helical cuts may extend between about 25 and 35 degrees about the axis, and the helical cuts may be axially separated by between about 0.001 and 0.1 inches.

Because the helical cuts take away material from the tube, the bending stiffness of the tube may decrease, and may allow the tube/catheter body to bend more easily (thereby increasing trackability). This change in bending stiffness may be at least partially determined by the arc of the helical cuts and posts, as well as the pitch of the helical cuts. The cut pattern just described can be characterized as a "three-post" pattern, which reflects that a ninety-degree region of uncut metal appears in the span of three post; i.e., $n \times 30° = 90°$, where n=3, the number of posts.

In comparison, a cut pattern characterized as "Right Hand Thread, 135° Cut/45° Uncut, 0.012" Pitch" may be used to describe a helical cut pattern that extends clockwise when viewed from the proximal end of the catheter body, in which the helical cuts thread 135 degrees about the longitudinal axis, posts between helical cuts extend 45 degrees about the axis, and wherein helical cuts are axially separated by 0.012 inches. This cut pattern can be characterized as a "two-post" pattern, which reflects that a ninety-degree region of uncut metal appears in the span of two post; i.e., $n \times 45° = 90°$, where n=2, the number of posts. It should be appreciated, however, that "Right Hand Thread, 135° Cut/45° Uncut, 0.012" Pitch" may be used to describe cut patterns in which helical cuts may thread between about 125 degrees and about 145 degrees about the longitudinal axis, the posts between helical cuts may extend between about 35 and 55 degrees about the axis, and the helical cuts may be axially separated by between about 0.001 and 0.1 inches.

As mentioned above, modifying the arc of the helical cuts, the arc of the posts, and/or the pitch of the helical cuts may alter the trackability of the catheter body. For example, increasing the arc of the helical cuts may decrease the bending stiffness and increase the trackability. Conversely, increasing the arc of the posts may increase the bending stiffness and decrease the trackability. Increasing the pitch may increase the bending stiffness while decreasing the pitch may decrease the bending stiffness. In some instances, it may be desirable for the pitch to be between about 0.006 inches and about 0.016 inches. A pitch below 0.006 inches may be difficult to achieve with conventional laser techniques as little uncut material remains, and in some instances a pitch above 0.016 inches may lose trackability.

By choosing a cut pattern, and/or by varying the cut pattern in a stepwise manner along the length of the catheter body, the bending stiffness of the catheter body can be incrementally reduced over its length to impart trackability, and may be done without diminishing the desired magnitudes of column stiffness, tensile stiffness, and torsional stiffness to a magnitude below that conducive to pushability, pullability, and torquability. As mentioned above, for some variations, the pitch may be varied between 0.006 inches and 0.016 inches to alter the bending stiffness.

The catheter bodies may have any number of zones/regions having different cut patterns (or in some zones, no cut pattern at all). For example, in the variation of atherectomy apparatus 900 shown in FIG. 9C, the catheter body 902 may comprise a first region 912 extending from the handle 906, a second region 914 extending distally from the first region 912, a third region 916 extending distally from the second region 914, a fourth region 918 extending distally from the third region 916, a fifth region 920 extending distally from the fourth region 918, and a sixth region 922 extending distally from the fifth region 920. In some variations each region may have a lower bending stiffness than the regions proximal to that region. In other variations, each region except the distal-most region may have a lower bending stiffness that the regions proximal to that region. Additionally, while shown in FIG. 9C as having six regions, it should be appreciated that the catheter bodies may include any number of regions (e.g., one, two, three, four, or five or more), and some or all of the regions may include a cut pattern such as those described here. For example, Table 1 includes one variation of cut patterns that may be utilized with a six-region catheter body 902 as shown in FIG. 9C:

TABLE 1

| Region | Axial Length | Cut Pattern (Right Hand Thread) | Pitch |
|---|---|---|---|
| 1 (Most Proximal) | 4.0" | Uncut | N/A |
| 2 | 47.04" | 100° Cut 30° Uncut | 0.012" |
| 3 | 2.0" | 110° Cut 30° Uncut | 0.010" |
| 4 | 2.0" | 110° Cut 30° Uncut | 0.008" |
| 5 | 1.5" | 110° Cut 30° Uncut | 0.006" |
| 6 (Most Distal) | .030" | Uncut | N/A |

Brickwork Cut Patterns

Figure 10A:
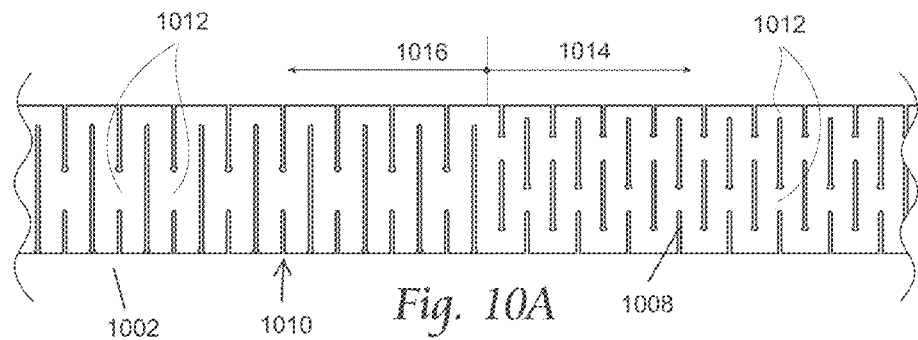
FIG. 10A is a side view of a portion of a variation of a catheter body suitable for use with the atherectomy systems described here.
Figure 10B:
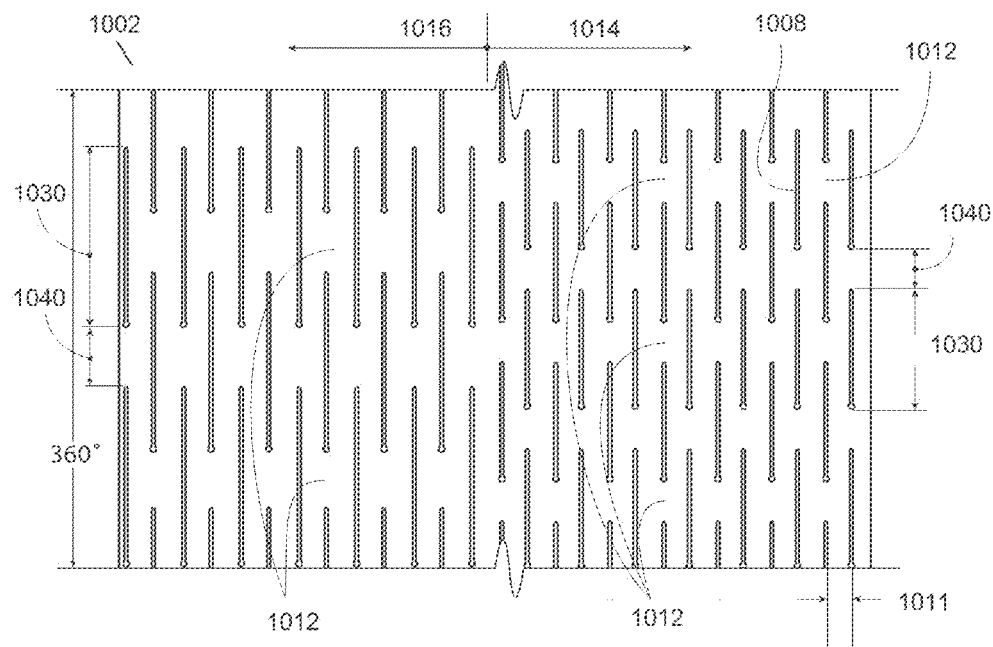
FIG. 10B depicts a plane view of the portion of the catheter body shown in FIG. 10A opened up into a sheet configuration.
Figure 10C:
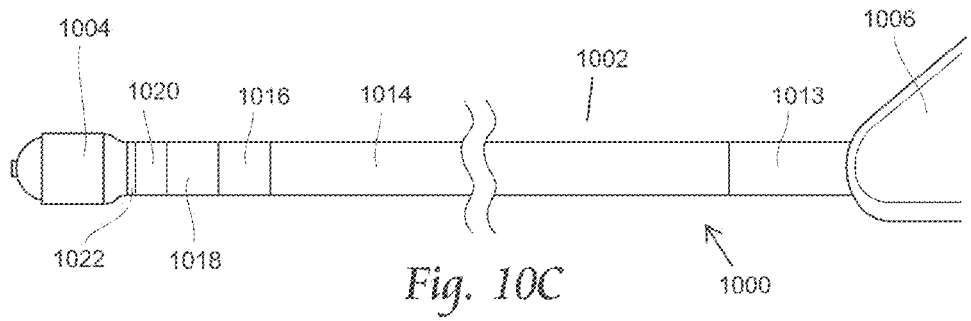
FIG. 10C depicts a side view of an atherectomy apparatus including the catheter body shown in FIGS. 10A and 10B.

In some variations, one or more zones may comprise a brickwork cut pattern. For example, FIGS. 10A-10C depict a variation of an atherectomy apparatus 1000 comprising a catheter body 1002, a cutter assembly 1004, and a handle 1006. Specifically, FIG. 10C shows a side view of the atherectomy apparatus 1000, FIG. 10A shows a side view of a section of the catheter body 1002, and FIG. 10B depicts a plane view of the section of the catheter body shown in FIG. 10A opened up into a sheet. As shown there, the catheter body 1002 may be formed from a tube and may comprise zones of cut patterns in the form of brickwork cuts 1008 (which may be laser cut) that thread around the longitudinal axis of the catheter body 1002. The brickwork cuts 1008 are generally normal to the longitudinal axis of the catheter body 1004, and may form rows 1010 of brickwork cuts 1008 along the catheter body 1004. In each row 1010, the brickwork cuts 1008 may be separated by uncut posts 1012, and rows 1010 are separated axially along the longitudinal axis. The pattern can be characterized in terms of the arc 1030 of the brickwork cuts 1008 about the longitudinal axis (in degrees), and the arc 1040 of the uncut region/posts 1012 about the longitudinal axis (also in degrees). The pattern can be further characterized in terms of the axial separation of the rows 1010 along the axis, which can also be called the "pitch" 1011. The pattern can also be characterized in terms of the offset between successive rows (in degrees). For example, in some variations, the positioning of the brickwork cuts 1008 and posts 1012 in a first row may be offset from those of an immediately adjacent row by about 45 degrees about the longitudinal axis (this may be referred to as "alternating brickwork" herein). In some variations, each row 1010 may comprise four equally-spaced brickwork cuts 1008, with successive rows offset in an alternating brickwork manner.

As discussed immediately above, a cut pattern characterized as "Brick Work Cut Pattern, 90° Cut/30° Uncut, 0.011" Pitch, Alternating" may be used to describe a brickwork cut pattern in which the brickwork cuts of a row extend 90 degrees about the axis, the posts of a row between brickwork cuts extend 30 degrees about the axis, successive rows are axially separated by 0.011 inches and a rotational offset by about 45 degrees. It should be appreciated that "Brick Work Cut Pattern, 90° Cut/30° Uncut, 0.011" Pitch, Alternating" may be used to describe cut patterns in which the brickwork cuts of a row may extend between about 80 degrees and about 100 degrees about the axis, the posts of a row between brickwork cuts may extend between about 20 degrees and about 40 degrees about the axis, successive rows may be axially separated by about 0.005 inches to about 0.2 inches and a rotational offset by between about 35 degrees and about 55 degrees.

The brickwork cut pattern, like the helical cut pattern, takes away material from the tube, which may reduce the bending stiffness of the tube and may allow the tube/catheter body to bend more easily (thereby increasing trackability). This change in bending stiffness may be at least partially determined by the arc of the brickwork cuts and posts, the pitch between rows, and the offset between rows.

The brickwork cut pattern just described can be characterized as a "three-post" pattern, which reflects that a ninety-degree region of uncut metal appears in the span of three posts; i.e., $n \times 30° = 90°$, where $n=3$, the number of posts.

In comparison, a cut pattern characterized as "Brick Work Cut Pattern, 135° Cut/45° Uncut, 0.011" Pitch, Alternating" may be used to describe a brickwork cut pattern in which the brickwork cuts of a row extend 135 degrees about the axis, the posts of a row between brickwork cuts extend 45 degrees about the axis, successive rows are axially separated by 0.011 inches and a rotational offset of 45 degrees. This brickwork cut pattern can be characterized as a "two-post" pattern, which reflects that a ninety-degree region of uncut metal appears in the span of two post; i.e., $n \times 45° = 90°$, where $n=2$, the number of posts. It should be appreciated that "Brick Work Cut Pattern, 135° Cut/45° Uncut, 0.011" Pitch, Alternating" may be used to describe cut patterns in which the brickwork cuts of a row may extend between about 125 degrees about 145 degrees about the axis, the posts of a row between brickwork cuts may extend between about 35 degrees and about 55 degrees about the axis, successive rows may be axially separated by between about 0.005 inches and about 0.2 inches and a rotational offset by between about 35 degrees and about 55 degrees.

As mentioned above, modifying the arc of the brickwork cuts, the arc of the posts, the pitch of the brickwork cuts, and/or the offset between rows may alter the trackability of the catheter body. For example, increasing the arc of the brickwork cuts may decrease the bending stiffness and increase the trackability. Conversely, increasing the arc of the posts may increase the bending stiffness and decrease the trackability. Increasing the pitch may increase the bending stiffness while decreasing the pitch may decrease the bending stiffness. In some instances, it may be desirable for the pitch to be between about 0.006 inches and about 0.016 inches. A pitch below 0.006 inches may be difficult to achieve with conventional laser techniques as little uncut material remains, and in some instances a pitch above 0.016 inches may lose trackability.

In transmitting an axial load (pushing or pulling) a catheter body having a brickwork pattern, as above described, may not undergo twisting, which may be experienced when the catheter body has a helically-cut pattern. Brickwork patterns may additionally exhibit an increased column, tensile, and torsional stiffness at a given bending stiffness.

By choosing a cut pattern, and/or by varying the cut pattern in a stepwise manner along the length of the catheter body, the bending stiffness of the catheter body can be incrementally reduced over its length to impart trackability, and may be done without diminishing the desired magnitudes of column stiffness, tensile stiffness, and torsional stiffness to a magnitude below that conducive to pushability, pullability, and torquability. As mentioned above, for some variations, the pitch may be varied between 0.006 inches and 0.016 inches to alter the bending stiffness.

The catheter bodies may have any number of zones/regions having different cut patterns (or in some zones, no cut pattern at all). For example, in the variation of atherectomy apparatus 1000 shown in FIG. 10C, the catheter body 1002 may comprise a first region 1013 extending from the handle 1006, a second region 1014 extending distally from the first region 1013, a third region 1016 extending distally from the second region 1014, a fourth region 1018 extending distally from the third region 1016, a fifth region 1020 extending distally from the fourth region 1018, and a sixth region 1022 extending distally from the fifth region 1020. In some variations each region may have a lower bending stiffness than the regions proximal to that region. In other variations, each region except the distal-most region may have a lower bending stiffness that the regions proximal to that region. Additionally, while shown in FIG. 10C as having six regions, it should be appreciated that the catheter bodies may include any number of regions (e.g., one, two, three, four, or five or more), and some or all of the regions may include a cut pattern such as those described here. For example, Table 2 includes one variation of cut patterns that may be utilized with a six-region catheter body 1002 shown in FIG. 10C:

TABLE 2

| Region | Axial Length | Square Cut Pattern (Brickwork) | Pitch |
|---|---|---|---|
| 1 (Most Proximal) | 4.0" | Uncut | N/A |
| 2 | 47.04" | 90° Cut 30° Uncut | 0.012" |
| 3 | 2.0" | 135° Cut 45° Uncut | 0.012" |
| 4 | 2.0" | 135° Cut 45° Uncut | 0.012" |
| 5 | 1.5" | 135° Cut 45° Uncut | 0.012" |
| 6 (Most Distal) | .030" | Uncut | N/A |

A catheter body having either a helical cut pattern or a brickwork cut pattern can be lined or jacketed with a polymeric material, and further may be treated to produce hydrophilic, hydrophobic, or drug binding (heparin, antimicrobial) properties.

Catheter Body Rotation

In some variations, the catheter body may be coupled to a post on the handle that is sized and configured to rotate in response to rotation of a control knob. For example, the atherectomy apparatus may comprise a rotation knob. Rotation of the knob may apply torque to the catheter body to selectively rotate the cutter assembly. An indexing mechanism may be provided to provide stepwise control, with tactile and/or audible feedback, so that the caregiver maintains knowledge of the rotational position of the cutter assembly without taking their eye off the radiographic or otherwise provided in-situ image.

It may also be possible to apply torque to the catheter body by rotating the handle itself. Selective rotation of the cutter assembly may thus be finely controlled by a combination of control knob manipulation and handle twisting.

The Cutter Assembly and Torque Shaft

As mentioned above, the atherectomy device may comprise a cutter assembly. The cutter assembly may comprise a ferrule, a cutter housing, and a cutter comprising at least one cutter element. In variations in which the cutter assembly comprises a ferrule, the cutter assembly may be joined to the distal end of the catheter body by the ferrule.

Figure 2:
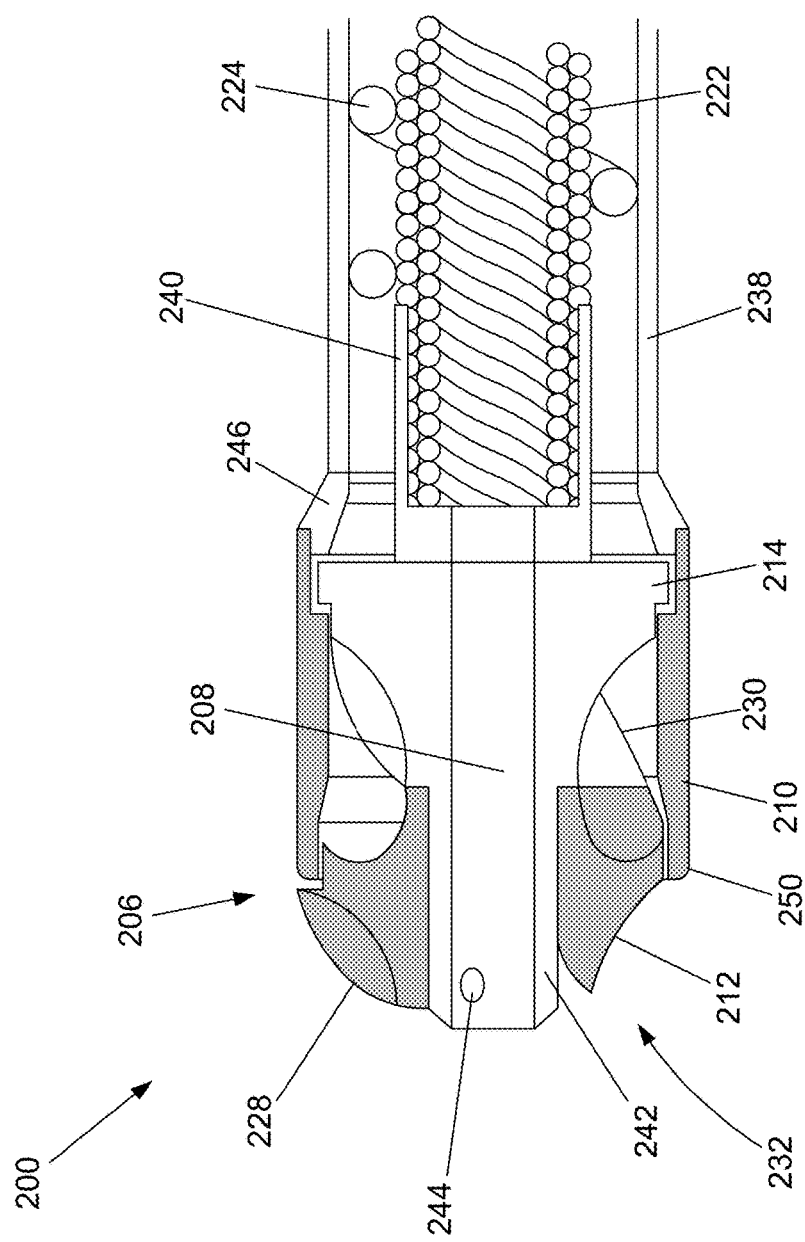
FIG. 2 depicts a cross-sectional side view of a distal portion of the atherectomy system shown in FIG. 1A.

FIG. 2 shows an example of a distal portion of an atherectomy device 200 having a cutter assembly 206. As shown there, the cutter assembly 206 may comprise a ferrule 246, a housing 210, and a cutter 232. The ferrule 246 may join one or more portions of the cutter assembly 206 (e.g., the housing 210) to the distal end of the catheter 238. The housing 210 may at least partially enclose the cutter 232, and in some instances may be a cylindrical housing having a distal opening. The cutter 232 may comprise a first, distal cutter 212 and a second, proximal cutter 214. The distal cutter 212 may comprise one or more cutting edges 228, which in some variations may at least partially project beyond the distal end of the housing 210. In some variations, at least a portion of the first, distal cutter 212 may have a diameter greater than or equal to the diameter of the housing 210. The proximal cutter 214 may be at least partially housed within the housing 210, and may comprise one or more cutting edges 230. In some variations, the cutting edges 230 of the proximal cutter 214 may be entirely enclosed within the housing 210. In some variations, the proximal cutter 214 may comprise a stem 242 extending from a base portion, and may further comprise a lumen 208 extending through the stem 242 and the base portion. In some variations, the cutter may comprise a port 244, which will be described in more detail below. Generally, the distal cutter 212 and the proximal cutter 214 may be physically coupled together (e.g., by adhesives, welding, or the like) for rotation in unison, although it should be appreciated that in other variations the cutter may be formed as a unitary body. The cutter 232 is discussed in more detail below.

A torque shaft 222, which may be positioned within the catheter 238, may rotationally connect a motor (not shown) to the cutter. Specifically, the motor may rotate the torque shaft 222, which may in turn rotate the cutter 232 within the housing 210 about the central axis of the catheter 238. Rotation of the cutter 232 may cause the distal cutter 212 and proximal cutter 214 to rotate, causing them to cut occlusive material and convey the occlusive material into the housing 210.

The housing 210 may or may not be able to rotate relative to the catheter 238. In variations where the housing 210 is able to rotate relative to the catheter 238, the ferrule 246 may join the cutter assembly 206 and the catheter 238 so as to allow relative rotation between the catheter 238 and the housing 210. In variations where the housing 210 is able to rotate relative to the catheter 238, the housing 210 may be configured to rotate at the same speed as the cutter 232, or it may be configured to rotate at a different speed than the cutter. Additionally, in variations where the housing 210 is able to rotate relative to the catheter 238, the housing 210 may be configured to rotate in the same direction or in the opposite direction from to the cutter 232. The distal end 250 of the housing 210 may in some variations comprise a sharp or beveled distal edge forming a cutting edge. In some variations in which the distal end 250 comprises a cutting edge, the distal end 250 may comprise an inner bevel, an outer bevel, or both an inner bevel and an outer bevel. It should be appreciated that in other variations, the distal end 250 of the housing 210 may not comprise a cutting edge. In some such variations, the distal end 250 may be rounded, which may reduce the possibility that the peripheral edges of the housing catch on the wall of an introducer during introduction therethrough and/or reduce the resistance felt by the atherectomy apparatus during advancement through the vasculature.

In some variations, the torque shaft 222 may comprise a conveyor member 224. In some of these variations, the conveyor member 224 may comprise an Archimedes screw. The conveyor member 224 may be located between the torque shaft 222 and the inner wall of the catheter 238, and may help to convey cut occlusive material proximally along the catheter 238. In some variations, the torque shaft 222 may comprise an end cap 240 at the proximal and/or distal ends of the torque shaft 222, wherein each end cap 240 may encase an end of the torque shaft 222, and which is discussed in more detail below.

Distal Cutter

Figure 3:
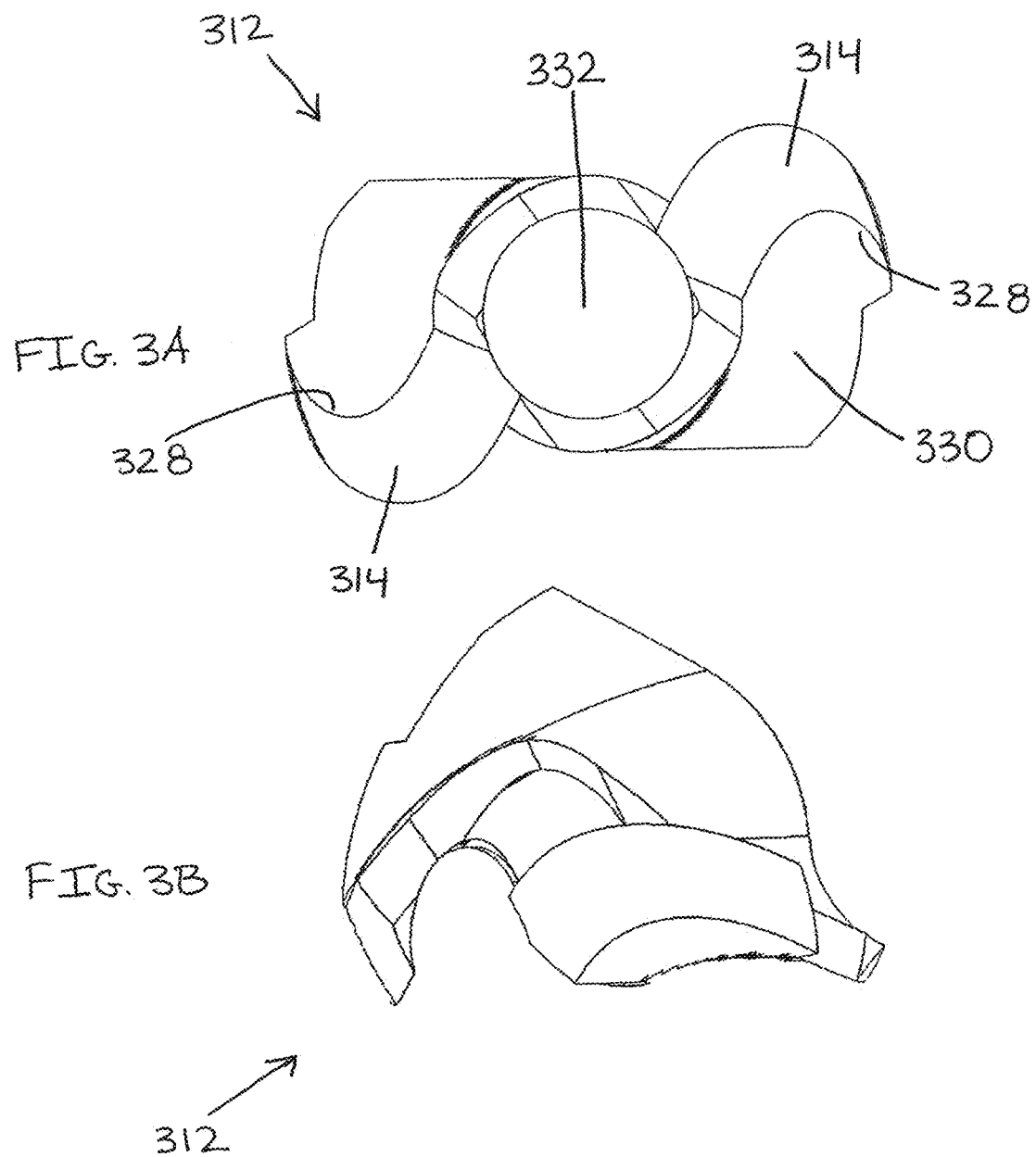
FIGS. 3A and 3B depict cross-sectional and perspective distal views, respectively, of a variation of a representative cutter as described here.

As mentioned above, in some variations, the cutter assembly may comprise multiple cutters. In some variations, the cutter may comprise a first, distal cutter and a second, proximal cutter. FIG. 3A shows a front view of the distal end, and 3B shows a perspective view, of an embodiment of a distal cutter 312. As shown there, the distal cutter 312 may comprise one or more helical cutting flutes 314, where each cutting flute 314 may form a cutting edge 328. While the cutting edges 328 of the helical cutting flutes 314 are shown as curving in a clockwise helical direction when viewed from the distal end, it should be appreciated that in other variations the cutting edges 328 of the cutting flutes 314 may have a counterclockwise helical curve when viewed from the distal end. Similarly, while the distal cutter 312 is shown has having two cutting flutes 314, it should be appreciated that in other variations, the distal cutter may comprise any suitable number of cutting flutes (e.g., one, two, three, four, or more cutting flutes).

It may be desirable to maximize the outer diameter of the distal cutter 312. Maximizing the outer diameter of the distal cutter 312 may maximize the area of occlusive material that may be cut by the cutter assembly. In some variations, the distal cutter 312 may have a maximum diameter greater than or equal to the housing. In these variations, the cutter 312 may cut a larger diameter of occlusive material, which may reduce the likelihood that the housing rubs against tissue during advancement while cutting, thereby facilitating advancement of the device by reducing resistance and in turn decreasing the force needed to advance the catheter.

The geometry of the cutting flutes 314 may be characterized with reference to a combination of angles (or ranges of angles), including rake angle, relief angle, and flute angle. The rake angle may be defined as the angle measured between (i) a radius drawn from the rotational axis of the distal cutter 312 to the most radially distant edge of the cutting edge 328 and (ii) a tangent drawn from the inner face 330 of the cutting flute 314. The rake angle may describe the angle of the cutting edge 328 relative to the material to be cut. The relief angle may be defined as the angle measured between (i) the tangent drawn from the most radially distant edge of the cutting edge 328 and (ii) the tangent drawn along the outer face of the cutting flute 314. Generally, a smaller relief angle may form a more tangential interface with a tissue surface during cutting, which may reduce the likelihood that a cutting edge may snag or otherwise catch on tissue during cutting. A larger relief angle may provide more aggressive cutting. The flute angle can be defined in terms of a relationship with the rake angle and the relief angle, as follows:

Flute Angle=90°−(Rake Angle)−(Relief Angle).

The magnitude of the flute angle may be an indication of how thick and sharp the cutting edge is. As shown in FIGS. 3A and 3B, in some variations the cutting flutes 314 may have a large positive rake angle (e.g., between about 60° and 80°); a relief angle between about 0° and about 10°; and a flute angle between about 0° and about 30°. As used here, "about" means±5%. As such, the cutting flute 314 may have an enlarged concave inner face 330 defining a trough- or scoop-shaped blade. Such a cutting flute design may cause the distal cutter 312 to encounter less resistance when the cutting flutes 314 are driven through occlusive material, and may aid in the cutting of hard or severe calcium and other challenging fibrous plaque morphologies. The cutting forces and power requirements for the distal cutter 312 may thus be reduced. Such a design may also allow a larger volume of occlusive material to be excised during each rotation of the distal cutter 312. Additionally or alternatively, such a design may allow the cutting flutes 314 to be formed with less material, and may improve the manufacturability of the distal cutter 312 by allowing the cutting flutes 314 to be formed with larger cutting tools. In some variations, the flutes 314 may draft outward from the distal end to the proximal end; that is, the flutes 314 may widen, such that they may be thicker on their proximal ends than on their distal ends.

The distal cutter 314 may comprise a central lumen 332, which may extend between the distal and proximal ends of the cutter 314. The lumen 332 may be configured to couple the distal cutter 314 and the proximal cutter and may be configured to receive a stem of the proximal cutter, as described in more detail below. The lumen 332 may also allow the guide wire to pass through the distal cutter 314.

FIGS. 11A-11D also depict an illustrative variation of a distal cutter 1100 suitable for use with the cutter assemblies described here. In some variations, the distal cutter 1100 may be machined from a hard metallic material (e.g., 440C stainless steel) and may have a generally hemispherical configuration that includes at least one helical flute 1102 (shown there as a right-hand twist, although it should be appreciated that the at least one helical flute 1102 may have a left-hand twist). While shown in FIGS. 11A-11D as having two helical flutes 1102, it should be appreciated that the distal cutter 1100 may comprise any suitable number of helical flutes 1102 (e.g., one, two, three, four, or more helical flutes). Each cutting flute may form a cutting blade 1103 having a cutting edge 1104.

The distal cutter may be machined to shape the structure of the helical flutes 1102 within the desired hemispherical geometry. When supported in an extended, distally projecting relationship relative to the cutter housing (e.g., by virtue of the connection to a proximal cutter, as described in more detail above), the hemispherical, fluted geometry may be sized and configured to optimize the capability of the cutting blade or blades to cut through and capture occlusive materials, while minimizing the risk of the cutting blade or blades grabbing or digging into tissue, wrapping tissue, and otherwise causing the motor to stall and overload.

The geometry of each flute may be purposely shaped for the above-mentioned purposes, and the flute geometry may be characterized with reference to a combination of angles (or ranges of angles), comprising a rake angle, a relief angle, a flute angle, and a helix angle. Additionally, while shown in FIGS. 11A-11D as having a hemispherical outer profile, it should be appreciated that the distal cutter may any external profile, such as an egg-shaped outer profile.

For each flute, the rake angle 1106 (best shown in FIG. 11C)—the angle measured between (i) a radius 1108 drawn from the rotational axis of the cutting blade 1110 to the most radially distant edge 1104 of the blade 1103 and (ii) a tangent 1110 drawn from the inner face of that blade 1103—may be positive (i.e., the inner face of the cutting blade slants inward or back from the cutting edge). The positive rake angle of each flute is preferably large, and in some instances may be between greater than about 20 degrees. In some of these variations, the rake angle is preferably greater than about 40 degrees. In some of these variations, the rake angle may be between about 60 degrees and 80 degrees (referred herein as a "high" rake angle). In some variations, the rake angle may be between 65 degrees and 75 degrees. In some variations, the rake angle may be about 70 degrees.

Generally, a device having a positive high rake angle may be well suited for cutting occlusive materials having less calcium, which may have a fibrous, fleshy, and/or rubbery consistency. The rubbery consistency may cause conventional cutters to deflect away from these materials, causing conventional devices to lose trackability, but a high rake angle helps a cutter slice into this tissue while minimizing deflection of the cutter. Conventional cutter machining techniques generally cannot produce a positive high rake angle cutter, and these cutters generally have a small rake angle (less than about 15 degrees). Additionally, a larger rake angle may decrease the structural integrity of a cutter, which may the cutter more likely to chip or break during use. The cutters described here, however, may allow for the benefits of high rake angle cutting while reducing the risk of cutter malfunction.

The rake angle of the cutter may be modified depending on the nature of the tissue to be cut. For example, a cutter assembly intended to cut hard, calcified occlusive materials having a higher calcium content, may be configured to have a negative rake angle (i.e., the inner face of the cutting blade may slant outward or forward of the cutting edge), which may be well suited for grinding or smashing hardened occlusive materials. It should be appreciated that a given cutter can be machined to incorporate cutting blades having both positive and negative rake angles or otherwise include combination of both cutting and grinding surfaces. For example, in some variations a cutter may comprise a distal cutter having a plurality of helical flutes, wherein at least one flute has a cutting edge having a positive rake angle and at least one flute has a cutting edge having a negative rake angle. In some of these variations, the helical flutes having cutting edges having a positive rake angle may have a positive rake angle greater than about 20 degrees (e.g., greater than about 40 degrees or about 70°±10°).

Figure 11D:
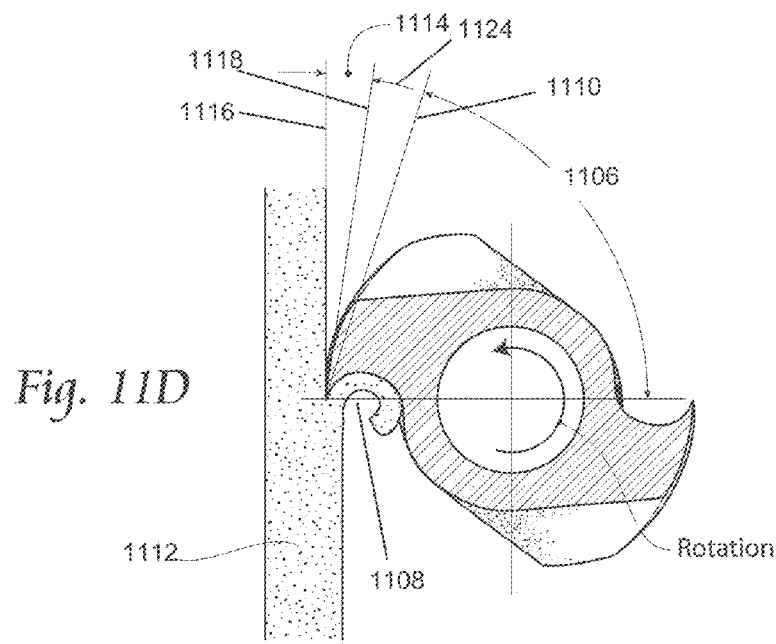
FIG. 11D is a cross-sectional view of the representative cutting element, like that shown in FIG. 11C, cutting into occlusive materials.

For each flute, the relief angle 1114—the angle measured between (i) the tangent 1116 drawn from the most radially distant edge 1104 of the cutting blade 1103 from radius 1108 and (ii) the tangent 1118 drawn along the outer face of the blade 1103—may preferably be a small angle less than or equal to about 10° (e.g., between about 0° and about 10°). In some of these variations, the relief angle may be about 0°. In some variations, it may be preferable to have a rake angle of about 70 degrees and a relief angle of about 0 degrees. In other variations, a helical flute may have a rake angle of about 60 degrees and a relief angle of about 10 degrees. The formation of a flute with a small relief angle may create a cutting edge 1104 that may make aggressive contact with the occlusive materials 1112 such as shown in FIG. 11D. Together with a large positive (high) rake angle, a small relief angle may lead to highly efficient cutting and capture of occlusive materials at the distal end of the cutter assembly, minimizing residue and embolization.

Given that, in a preferred embodiment, the rake angle may be in a range between about 60° and 80°; the relief angle may be in a range between of about 0° and 10°, the flute angle may be in range between about 0° and about 30°. Maximizing the rake angle and minimizing the relief angle to achieve efficient cutting conditions may result in a cutter geometry having a reduced flute angle. Accordingly, it may be desirable that the distal cutter be machined from a hard metallic material to include at a cutting edge that is a sharp as possible. In some variations, is may also be desirable to coat the cutting blade with a biocompatible, highly lubricious material with a low coefficient of friction (preferably no greater than 0.5) to help keep the cutting blade sharp during use. In these variations, coating materials such as titanium nitride or diamond-like carbon (DLC) may be used.

In the variation of the distal cutter 1100 shown in FIGS. 11A-11D, each flute 1102 of the distal cutter 1100 may comprise a helical cut. The helix angle 1126 may be defined as the angle between (i) the rotational axis 1128 of the cutting blade 1103 and (ii) a tangent 1130 drawn along the inner face the cutting blade 1103. The magnitude of the helix angle is indicative of the capability of the cutting blade to transport cut occlusive material proximally along the cutting blade and into the housing. In some variations, each flute 1102 of the distal cutter 1100 may have a helix angle 1102 between about 30° and 60°. A helix angle below 30° may increase the likelihood the distal cutter 1100 may overload with occlusive material and stall, while a helix angle above 60° may diminish the cutting efficiency of the distal cutter 1100.

Proximal Cutter

As mentioned above, the cutter assembly may comprise a proximal cutter. In variations that include a proximal cutter, the proximal cutter may be machined from a hard metallic material (e.g., 17-4 stainless) to include helical cutting flutes. The cutting flutes may be configured to have the same rake angle, relief angle, flute angle, and helix angle as the flutes of the distal cutter. In some variations, the above-mentioned geometries of the proximal and distal cutters may be identical, except that the proximal has more flutes than the distal cutter. In some of these variations, the proximal cutter may have double the number of flutes of the distal cutter; that is, four flutes.

Figure 12:
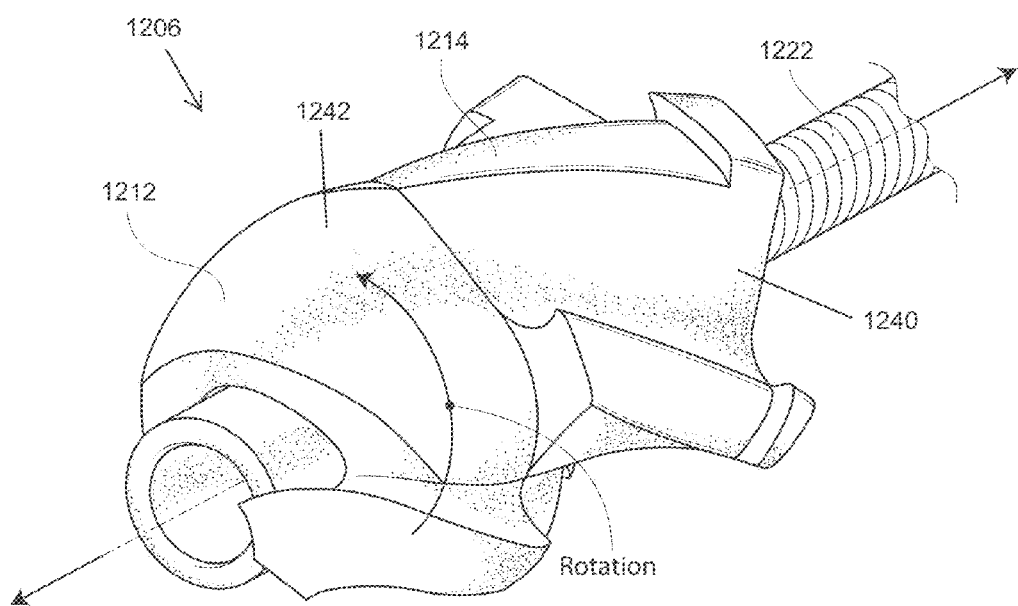
FIG. 12 depicts a distal perspective view of a variation of a cutter comprising distal and proximal cutters.

FIG. 12 shows a perspective view of a cutter assembly 1206, in which the distal 1212 and proximal 1214 cutters may be joined together (e.g., by adhesive or welding) in a rotationally aligned condition. In the aligned condition, two opposing cutting flutes 1240 of the proximal cutter 1214 may be rotationally aligned with the two opposing cutting flutes 1242 of the distal cutter 1212. Their geometries may be matched during machining, and may act to cut and conveyed occlusive material proximally by the distal cutter into the housing and further convey the occlusive material more proximally into contact with the additional cutting blades of the proximal cutter.

The cutter assembly 1206 shown in FIG. 12 may provide a two-stage cutting action. Generally, the distal cutter 1212 may cut occlusive material and convey the material to the second proximal cutter 1214. The proximal cutter 1214 may further cut or macerate the occlusive materials into smaller particles. During both cutting actions, the occlusive materials may be continuously captured within the housing and conveyed proximally away from the targeted intravascular site. When the first and second cutter elements rotate, the helical cutting surfaces formed by the flutes may cut occlusive materials in the blood vessel and may convey the occlusive material from the blood vessel into the housing through the action of the helical flutes, and may do so without the assistance of any vacuum aspiration.

Figure 6:
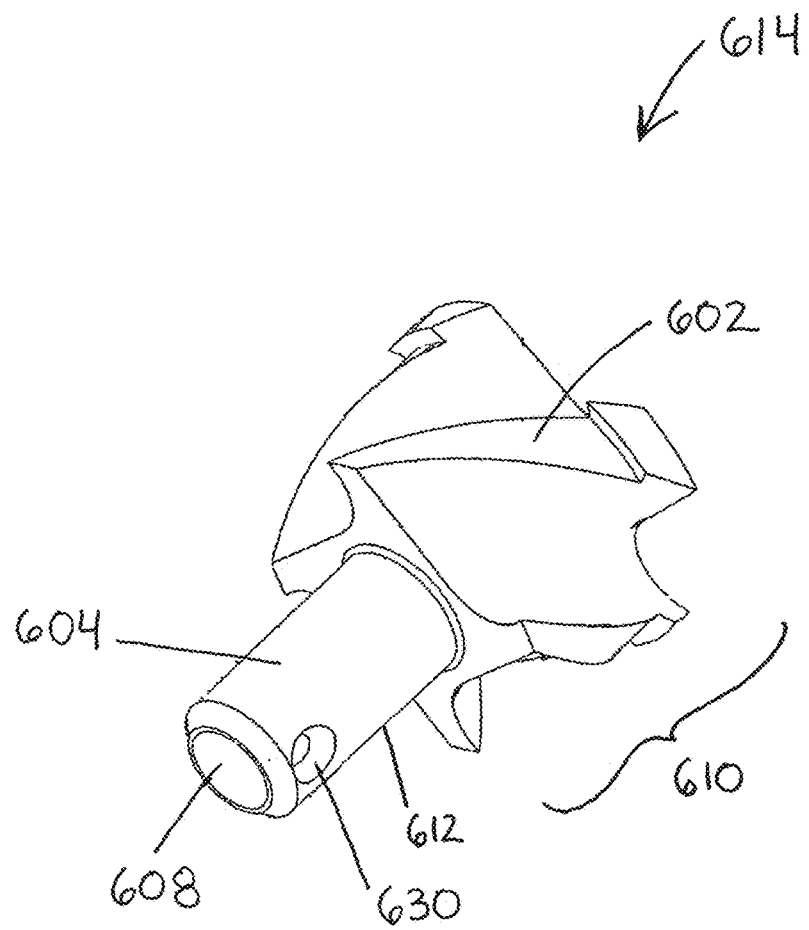
FIG. 6 depicts a perspective view of a variation of a cutter as described here.

FIG. 6 shows a perspective view of a variation of a proximal cutter 614 that may be used with the atherectomy devices described herein. As shown there, the proximal cutter 614 may comprise a base portion 610 comprising a plurality of cutting flutes 602 and a stem 604 extending distally from a distal end of the base portion 610. While the variation of FIG. 6 is shown having four cutting flutes 602, it should be appreciated that the proximal cutter may comprise any suitable number of cutting flutes (e.g., one, two, three, four, five, six, or more). In some variations, the proximal cutter 614 may comprise more cutting flutes than the distal cutter. In other variations, the proximal cutter 614 and the distal cutter may have the same number of cutting flutes. Generally, the stem 604 may allow the distal cutter to be connected to the proximal cutter 614 (e.g., by positioning the stem 604 through a central lumen of the distal cutter). In some variations, the stem 604 may have a cylindrical shape with a diameter equal to an inner diameter of the central lumen of the distal cutter. In other variations, one or more members may be positioned between the stem 604 and the inner lumen of the distal cutter. The proximal cutter 614 may also comprise a lumen 608, which may extend through the stem 604 and the base portion 610 of the proximal cutter 614, and through which a guide wire may be advanced.

In some variations, the cutter assembly (or other elements of the device, as described below) may be configured to reduce the amount of plaque or other tissue that may become trapped within the guide wire lumen. During advancement or manipulation of the atherectomy apparatus, material (e.g., plaque or other tissue) may enter the guide wire lumen through a distal opening at the end of the cutter assembly. In some such variations, the cutter assembly may comprise an opening or port that allows such material to exit the guide wire lumen after entering. This opening or port may be located proximally to the distal opening of the guide wire lumen, and may in some cases be located such that material existing through the opening or port may be recaptured by the cutter assembly and removed through the intended conveyance mechanism of the device.

The proximal cutter 614 of FIG. 6 illustrates one such opening or port. As shown there, the stem 604 of proximal cutter 614 may comprise a wall 612 surrounding the lumen 608. The lumen 608 may comprise a distal opening located at the distal end of the cutter assembly. The stem 604 may comprise a port 630, which may be an opening extending through the wall 612 from the lumen 608 to an outer surface of the stem 604. As such, the port 630 may be located proximally to the distal opening of the lumen 608. In variations comprising a port 630, the port 630 may help allow such trapped plaque or other tissue to exit the lumen 608. More specifically, plaque or other material may enter the distal opening of the lumen 608, travel proximally down the lumen 608, and then travel outwardly through the port 630 to exit the lumen 608. The plaque or other material may then enter the space between the cutter and the housing and may be captured by a cutting flute 602 and be conveyed proximally along the catheter through the space between the catheter and the torque shaft. The port 630 may have any suitable configuration to allow material trapped within the lumen 608 to be transported out of the lumen 608. In some variations, the port 630 may extend through the wall 612 of the stem 604 near the distal end of the stem 604. While the port 630 is shown as having a circular cross-section, it should be appreciated that the port 630 may have any suitable cross-sectional shape (e.g., circular, elliptical, rectangular, ovoid, or the like). It should be appreciated that while one port 630 is shown in FIG. 6, in other variations the stem 604 may comprise any suitable number of ports 630 (e.g., two, three, or four or more ports 630).

When the distal cutter is connected to the proximal cutter 614 via the stem 604, as described above, the distal cutter may cover a portion of the stem 604 and may leave a portion of the stem 604 exposed (e.g., between portions of the flutes of the distal cutter). In some of these variations, the port 630 may be located on a portion of the stem 604 that is exposed by the distal cutter. In others of these variations, the port 630 may be located on a portion of the stem 604 that is covered by the distal cutter. In these variations, the port 630 may be aligned with another port extending through the distal cutter, such that the aligned ports create a contiguous opening from the lumen 608 of the proximal cutter 614, through the wall 612 of the stem 604, and through the distal cutter to the space between the cutter and the housing.

In some instances, the port 630 may be angled proximally—that is, the port 630 may extend through the wall 612 from an interior opening in the inner surface of the wall 612 to an exterior opening in the outer surface of the wall 612, where the interior opening is located distal to the exterior opening. Proximal angling of the port 630 may promote transfer of material from the lumen 608 into the space between the cutter and the housing while reducing the likelihood that material captured in the housing will enter the lumen 608 through the port 630. In other variations, the port 630 may be angled distally—that is, the port 630 may extend through the wall 612 from an interior opening in the inner surface of the wall 612 to an exterior opening in the outer surface of the wall 612, where the interior opening is located proximal to the exterior opening. In still other variations the port 630 may extend straight through the wall 612 of the stem 604—that is, the port 630 may extend through the wall 612 from an interior opening in the inner surface of the wall 612 to an exterior opening in the outer surface of the wall 612, where the interior opening and exterior opening are located along the stem 604 at the same position along the distal/proximal axis.

In some instances, the cross-sectional area of the port 630 may be tapered, such that the cross-sectional area of the port 630 increases from the interior opening in the inner surface of the wall 612 to the exterior opening in the outer surface of the wall 612. Such tapering of the port 630 may promote transfer of material from the lumen 608 into the space between the cutter and the housing, and it may resist transfer of material into the lumen 608. However, it should be appreciated that in other variations the cross-sectional area may be tapered in the other direction, such that the cross-sectional area of the port 630 decreases from the interior opening in the inner surface of the wall 612 to the exterior opening in the outer surface of the wall 612. In still other variations the cross-sectional area may not be tapered, such that the cross-sectional area of the port 630 is substantially constant through the wall 612 from the interior opening to the exterior opening. In some instances, it may be desirable to minimize the cross-sectional area of the port 630. For example, the cross-sectional area of the port 630 (at at least one position between the interior opening and exterior opening) may in such instances have a cross-sectional area that is less than about 50% of the cross-sectional area of the stem 604. This may decrease the likelihood of plaque entering the lumen 608 through the port 630. In some instances in which a guide wire is positioned through the lumen 608, introduction of plaque into the lumen 608 through the port 630 may also be resisted by the narrow gap between the guide wire and the inner surface of the wall 612 of the stem 604.

In other variations, the atherectomy devices described here may additionally or alternatively comprise other features configured to reduce the amount of plaque or other tissue that may become trapped within the guide wire lumen, for example by preventing such material from entering the lumen, or by allowing such tissue to exit the lumen. For example, in some variations the atherectomy devices may comprise a lip seal configured to contact the guide wire. This may prevent plaque or other tissue from entering the lumen. As another example, in some variations material (e.g., trapped plaque or other tissue) may be pushed out of the lumen by fluid (e.g., saline) pumped out through the lumen. After the material is pushed out of the lumen, the material and fluid may be captured by a cutting flute (i.e., between cutter and the housing) and conveyed proximally along the catheter through the space between the catheter and the torque shaft. In some variations in which fluid is pumped out through the lumen, the torque shaft may be jacketed in order to seal the torque shaft. In some variations in which fluid is pumped out through the lumen, an external pressure cuff bag attached to the atherectomy device (e.g., attached to the proximal end of the handle) may provide pressure for pumping the fluid.

The size of the cutter assembly, and in turn the sizes of the distal and proximal cutters, may be different based on the intended anatomical locations for use. For example, the size of the cutter assembly may be limited by the intended intravascular path and the region targeted for treatment, to help reduce the likelihood that the cutter assembly will cut or otherwise damage the vessel wall. In some of the variations described here, a cutter assembly sized for introduction through a 7F guide sheath may have an outer diameter of about 2.4 mm (which, in some variations, may be larger than the outer diameter of the connected catheter). A cutter assembly having such an outer diameter may be used, for example, for access to the larger vessels above the knee (e.g., vessels between about 4 mm and about 7 mm). In other variations, a cutter assembly sized for introduction through a 5F or 6F guide sheath may have an outer diameter of about 1.8 mm to about 2.2 mm (which, in some variations, may be larger than the outer diameter of the connected catheter). A cutter assembly having such an outer diameter may be used, for example, for access to the smaller vessels at or below the knee (e.g., vessels between about 2.5 mm and about 4 mm). In yet other variations for use in even smaller vessels, a cutter sized for introduction through a 4F guide sheath may have an outer diameter of about 1.0 mm (which, in some variations, may be larger than the outer diameter of the connected catheter).

Torque Shaft

As described above, a torque shaft may connect a motor to the cutter. FIGS. 7A and 7B show side and cross-sectional side views, respectively, of a variation of a torque shaft 722 that may be used with the atherectomy devices described herein. Generally, the torque shaft 722 may comprise a coiled shaft 724 having a central lumen 728. In some variations, the coiled shaft 724 may be wound in the same direction as the intended direction of rotation of the torque shaft 722. In some variations, the coiled shaft 724 may have a multi-filar design. The central lumen 728 may be sized to accommodate the passage of a guide wire therethrough, and may communicate with a central lumen of the cutter assembly. The torque shaft 724 may be coupled at or near its distal end to a cutter of a cutter assembly, and the torque shaft 724 may be coupled at or near its proximal end to a motor (either directly, or through one or more connectors). In some variations, the torque shaft 722 may be coupled to the cutter assembly and/or the motor via end caps 726. However, while the variation shown in FIGS. 7A and 7B comprises both a distal end cap 726 and a proximal end cap 726, it should be appreciated that in other variations, the atherectomy devices described herein may comprise only a distal end cap 726, may comprise only a proximal end cap 726, or may comprise neither a distal end cap 726 nor a proximal end cap 726. The end caps 726 are described in more detail below.

The torque shaft may be fabricated from any suitable material, preferably one or more materials that may be consistent with the pushability, pullability, torquability, and trackability of the catheter body, as described above. For example, the torque shaft may comprise a metal braid and/or one or more metal coils, and one or more portions of the torque shaft embedded in a polymer, e.g., PEBAX, polyurethane, polyethylene, fluoropolymers, parylene, polyimide, PEEK, and/or PET. In some variations, the torque shaft may be made from a rigid material such as plastic, rendered flexible by incorporation of a spiral relief or groove.

Figure 4:
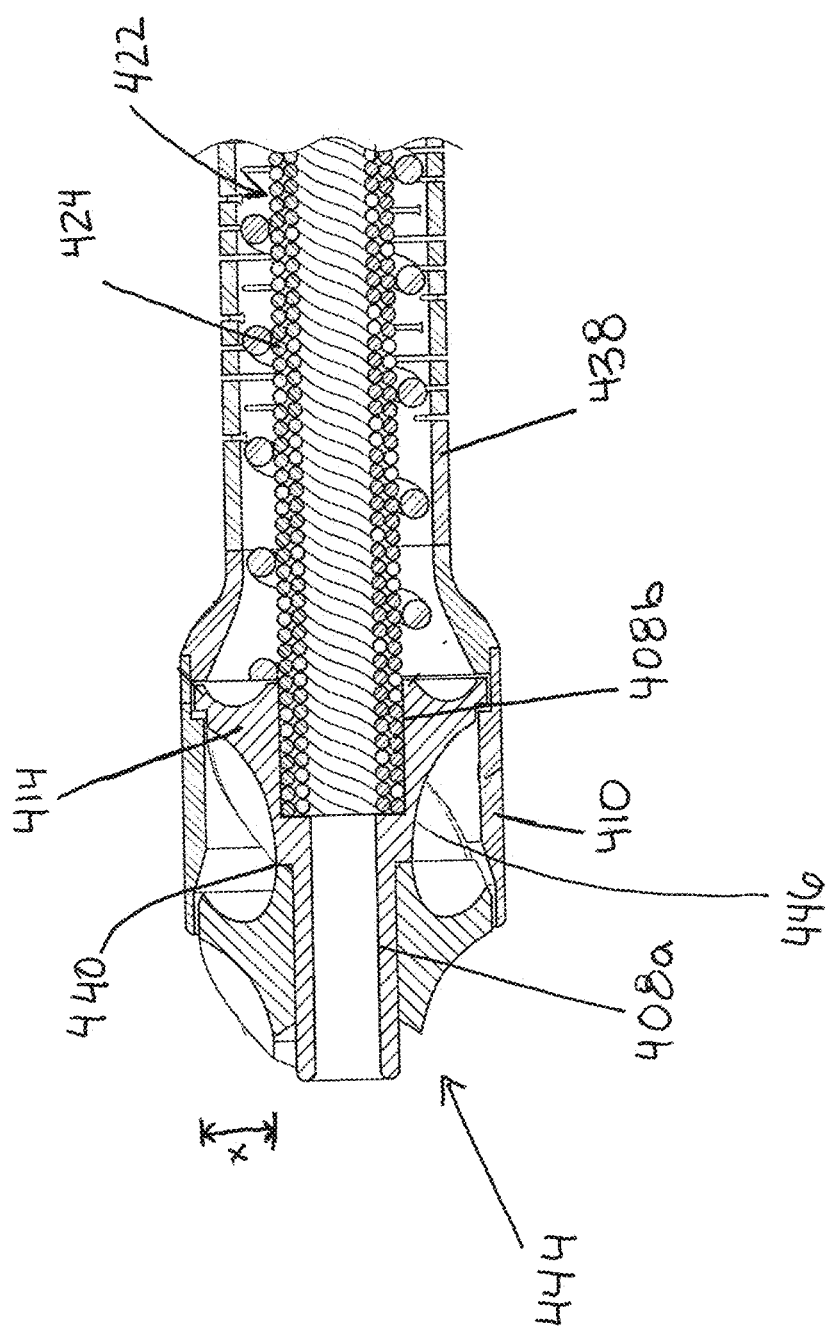
FIG. 4 depicts a cross-sectional view of a distal portion of a variation of an atherectomy system.

The torque shaft may be coupled to the cutter assembly via different methods. The manner of attachment between the cutter and the torque shaft may affect the usable area of a cutter for cutting and conveying occlusive material for a given diameter cutting assembly. In some variations, the torque shaft may be coupled at its distal end to the cutter via a counterbore, as shown in FIG. 4. As shown there, the proximal cutter 414 may comprise a lumen 408 having a distal portion 408a and a counterbore 408b. Generally, the lumen 408 is sized to receive a guide wire, and the counterbore 408b may have an enlarged diameter relative to the distal portion 408a of the lumen 408 to receive the distal end of the torque shaft 422. The torque shaft 422 may thus be coupled to the lumen 408 by the distal end of the coiled shaft 424 of the torque shaft 422 being attached to the counterbore 408b. The distal end of the coiled shaft 424 may be attached to the counterbore 408b via any suitable method, such as but not limited to soldering, crimping, or using adhesives.

Generally, the proximal cutter 414 may include a minimum thickness surrounding the lumen 408 (hereinafter referred to as a "waist" 440), and the cutting flutes of the proximal cutter may extend from the waist 440 to an inner diameter of the housing. Generally, the area between the waist and the inner diameter of the housing may be available for cutting and/or conveying, and is hereinafter referred to as the "active space" of the proximal cutter. When the waist 440 has a circular cross-section, the active space may be a hollow cylindrical shape having a wall thickness (labeled "x" in FIG. 4). In contrast, the remaining area within the housing 410 (e.g., the waist 440 and lumen 408) may not directly engage in cutting or conveyance of occlusive material (inadvertent introduction of material into the lumen 408 is not considered conveyance as described here), and is thus referred to hereinafter as "dead space." In some instances, the diameter of the base portion 446 of the proximal cutter 414 at the waist 440 may be dictated by the minimum material thickness between the lumen 408 of the proximal cutter 414 and the waist 440 to provide structural integrity to the proximal cutter 414. For example, in some variations where the lumen 408 includes a counterbore 408b, the inner diameter of the housing 410 may be equal to about 0.084 inches, and the diameter of the proximal cutter 414 at the waist 440 may be about 0.044 inches, making the thickness of the active space (i.e., "x") equal to about 0.040 inches and the cross-sectional area of the active space equal to about 0.0040 square inches. As such, the active space may make up about 73% of the area within the housing 410 (hereinafter referred to as the "active space percentage"). As another example of a variation where the lumen 408 includes a counterbore 408b, the inner diameter of the housing 410 may be equal to about 0.077 inches, and the diameter of the proximal cutter 414 at the waist 440 may be about 0.037 inches, making the thickness of the active space (i.e., "x") equal to about 0.040 inches and the cross-sectional area of the active space equal to about 0.0036 square inches. As such, the active space percentage may be about 77%. As yet another example of a variation where the lumen 408 includes a counterbore 408b, the inner diameter of the housing 410 may be equal to about 0.060 inches, and the diameter of the proximal cutter 414 at the waist 440 may be about 0.038 inches, making the thickness of the active space (i.e., "x") equal to about 0.022 inches and the cross-sectional area of the active space equal to about 0.0017 square inches. As such, the active space percentage may be about 60%. As yet another example of a variation where the lumen 408 includes a counterbore 408b, the inner diameter of the housing 410 may be equal to about 0.034 inches, and the diameter of the proximal cutter 414 at the waist 440 may be about 0.024, making the thickness of the active space (i.e., "x") equal to about 0.010 inches and the cross-sectional area of the active space equal to about 0.00046 square inches. As such, the active space percentage may be about 50%.

Figure 5:
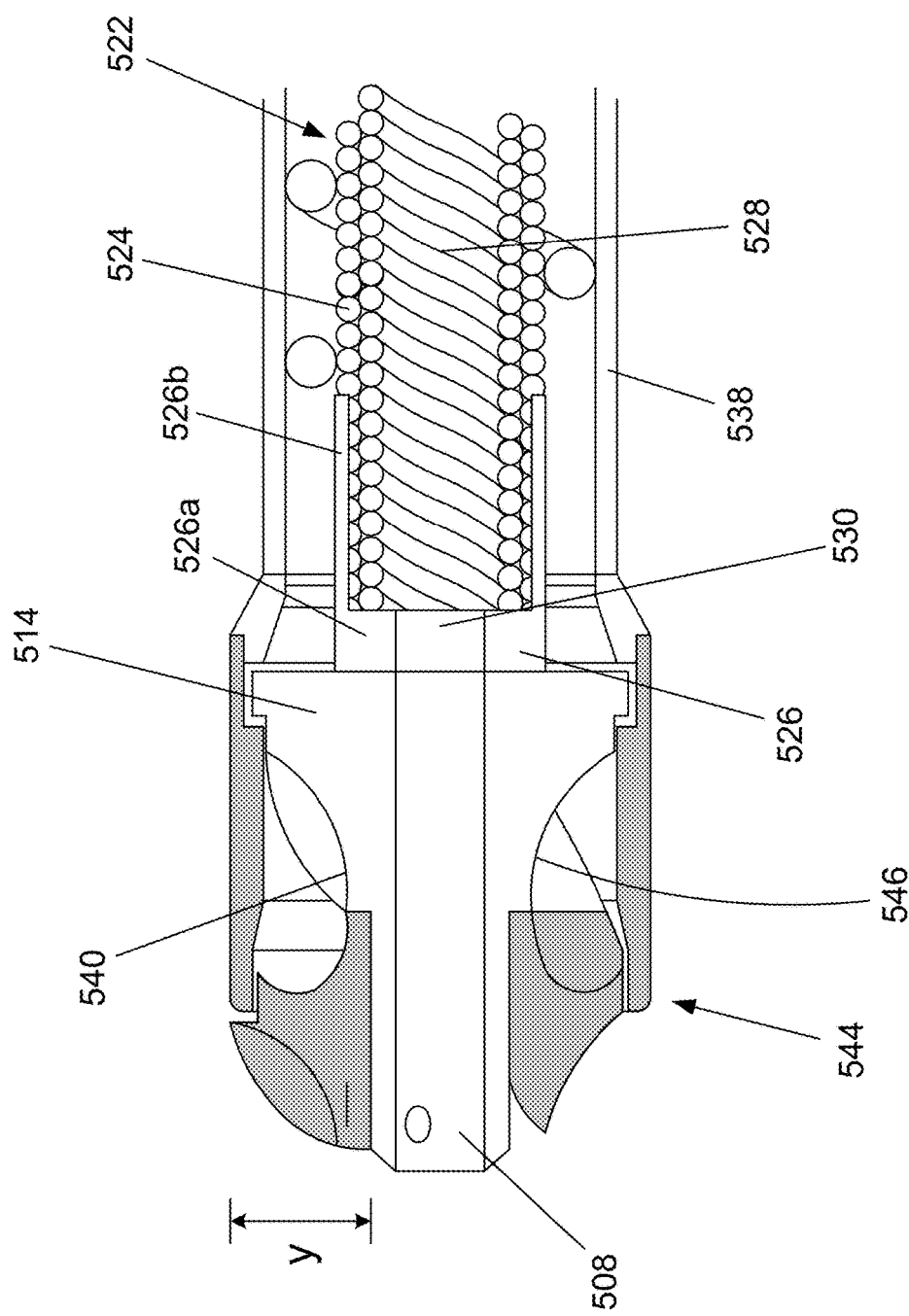
FIG. 5 depicts a cross-sectional view of a distal portion of another variation of an atherectomy system.

In other variations, the torque shaft may be coupled at its distal end to the cutter via an end cap, such as shown in FIG. 5. As shown there, the end cap 526 may have a hollow cylindrical shape with a distal portion 526a and a proximal portion 526b. The wall thickness of the distal portion 526a may be greater than the wall thickness of the proximal portion 526b, while the outer diameters of the distal portion 526a and proximal portion 526b may be the same. Thus, the inner diameter of the distal portion 526a may be less than the inner diameter of the proximal portion 526b. The inner diameter of the proximal portion 526b may be approximately the same as the outer diameter of the coiled shaft 524 of the torque shaft 522, while the inner diameter of the distal portion 526a may be approximately the same as the diameter of the lumen 528 of the torque shaft 522 and/or the lumen 508 of the proximal cutter 514. Thus, the proximal portion 526b of the end cap 526 may be sized and configured to fit over the distal end of the coiled shaft 524 of the torque shaft 522, while the distal portion 526a of the end cap 526 may be sized and configured to sit adjacent to the distal end of the coiled shaft 524. When the end cap 526 is positioned over the distal end of the coiled shaft 524, a guide wire may be able to pass through the lumen 508 of the proximal cutter, through the central lumen 528 of the torque shaft, and through the end cap 526.

In some variations, the outer diameter of the coiled shaft 524 and the inner diameter of the proximal portion 526b of the end cap 526 may be between about 0.01 and about 0.05 inches. In other variations, this diameter may be between about 0.02 and about 0.04 inches. In other variations, this diameter may be about 0.03 inches. In other variations, this diameter may be greater than 0.05 inches. In some variations, the proximal end 526b of the end cap 526 may have a wall thickness between about 0.001 inches and about 0.002 inches. In other variations, the proximal end 526b of the end cap 526 may have a wall thickness of about 0.0015 inches. In other variations, the proximal end 526b of the end cap 526 may have a wall thickness between about 0.002 inches and about 0.005 inches. In other variations, the proximal end 526b of the end cap 526 may have a wall thickness between about 0.003 inches and about 0.004 inches. In other variations, the proximal end 526b of the end cap 526 may have a wall thickness greater than about 0.005 inches. The end caps 526 may be fabricated from any suitable material, such as but not limited to stainless steel, titanium, and cobalt chromium alloys. The end caps 526 may be fabricated using any suitable manufacturing methods, such as but not limited to extrusion, stamping, or injection molding. In some variations, the end cap 526 may be attached to the distal end of the coiled shaft 524 via soldering or the like. In some variations, the coiled shaft 524 may have had accurate (concentric) centerless grinding of its distal end, which may enable more precise attachment of the end cap 526.

As shown in FIG. 5, in variations of the torque shaft 522 having an end cap 526, the torque shaft 522 may be attached to the cutter assembly 544 via the end cap 526. More particularly, the distal surface of the distal end 526a of the end cap 526 may be attached to the proximal end of the proximal cutter 514. In some variations, the proximal cutter 514 may comprise a flat proximal surface for attachment of the end cap 526. The end cap 526 may be attached to the cutter assembly 544 using any suitable method, such as laser welding, resistance welding, or the like. By attaching the torque shaft 522 to the cutter assembly 544 at the proximal surface of the proximal cutter 514, the proximal cutter may not require a counterbore as described in FIG. 4, which may in turn increase the active space of the cutter assembly 544. More particularly, the smaller diameter of the lumen 508 of the proximal cutter (e.g., compared to a counterbore) may allow for a waist 540 having a smaller diameter. In instances where the waist 540 has a circular cross-section, the active space may thus comprise a hollow cylindrical shape having a wall thickness indicated by the "y" in FIG. 5. In contrast, dead space (e.g., the thickness of the waist 540 and the lumen 508) may be reduced. For example, the waist 540 may have the same minimum material thickness as described with respect to the waist 440 of the proximal cutter 414 in FIG. 4. In some of these variations where the inner diameter of the housing 510 may be equal to about 0.084 inches, the diameter of the proximal cutter 514 at the waist 540 may be about 0.034 inches, making the thickness of the active space (i.e., "y") equal to about 0.050 inches and the cross-sectional area of the active space equal to about 0.0046 square inches. As such, the active space may make up about 84% of the area within the housing 510 (i.e., an 84% active space percentage). An another example of a variation where the torque shaft is attached to the cutter assembly via an end cap, the inner diameter of the housing 510 may be equal to about 0.077 inches, and the diameter of the proximal cutter 514 at the waist 540 may be about 0.034 inches, making the thickness of the active space (i.e., "y") equal to about 0.043 inches and the cross-sectional area of the active space equal to about 0.0037 square inches. As such, the active space percentage may be about 81%. As yet another example of a variation where the torque shaft is attached to the cutter assembly via an end cap, the inner diameter of the housing 510 may be equal to about 0.060 inches, and the diameter of the proximal cutter 514 at the waist 540 may be about 0.034 inches, making the thickness of the active space (i.e., "y") equal to about 0.026 inches and the cross-sectional area of the active space equal to about 0.0019 square inches. As such, the active space percentage may be about 68%. As yet another example of a variation where the torque shaft is attached to the cutter assembly via an end cap, the inner diameter of the housing 510 may be equal to about 0.034 inches, and the diameter of the proximal cutter 514 at the waist 540 may be about 0.020 inches, making the thickness of the active space (i.e., "y") equal to about 0.014 inches and the cross-sectional area of the active space equal to about 0.00059 square inches. As such, the active space percentage may be about 65%.

Variations of the atherectomy devices described herein in which the torque shaft is attached to the cutter assembly via an end cap may have a higher active space percentage than the variations in which the torque shaft is attached to the cutter assembly via a counterbore. For example, a comparison of the examples is illustrated in Table 3 below.

TABLE 3

| Attachment via | Inner Housing Diameter (inches) | Waist Diameter (inches) | Active Space (square inches) | Active Space Percentage (%) |
|---|---|---|---|---|
| Counterbore | 0.084 | 0.044 | 0.0040 | 73 |
| End Cap | 0.084 | 0.034 | 0.0046 | 84 |
| Counterbore | 0.077 | 0.037 | 0.0036 | 77 |
| End Cap | 0.077 | 0.034 | 0.0037 | 81 |
| Counterbore | 0.060 | 0.038 | 0.0017 | 60 |
| End Cap | 0.060 | 0.034 | 0.0019 | 68 |
| Counterbore | 0.034 | 0.024 | 0.00046 | 50 |
| End Cap | 0.034 | 0.020 | 0.00059 | 65 |

Attachment of the torque shaft to the cutter assembly via an end cap may thus result in an increase of the conveyance area relative to the area within the housing. For example, when the inner diameter of the housing is 0.084 inches, the use of end caps may increase the conveyance area up to about 15% as compared to a design without end caps, and may increase the conveyance area up to about 11% of the area within the housing. As another example, when the inner diameter of the housing is 0.077 inches, the use of end caps may increase the conveyance area up to about 5% as compared to a design without end caps, and may increase the conveyance area up to about 4% of the area within the housing. As yet another example, when the inner diameter of the housing is 0.060 inches, the use of end caps may increase the conveyance area up to about 11% as compared to a design without end caps, and may increase the conveyance area up to about 7% of the area within the housing. As yet another example, when the inner diameter of the housing is 0.034 inches, the use of end caps may increase the conveyance area up to about 30% as compared to a design without end caps, and may increase the conveyance area up to about 15% of the area within the housing. Conversely, attachment of the torque shaft to the cutter assembly via an end cap may decrease the dead space as a percentage of the area within the housing. This may improve cutting and conveyance of cut material through the cutter to the conveyor member. It should be appreciated that such an increase may be achieved for cutter assemblies having other dimensions than those described above. It should also be appreciated that in some variations, a torque shaft may be attached to a cutter assembly via both an end cap and a counterbore. That is, an end cap may be attached to the distal end of the coiled shaft of the torque shaft, which may in turn be attached to the proximal cutter via a counterbore. Such variations may have a smaller active space percentage than variations attached via only an end cap or via only a counterbore.

In some variations, the proximal end of the torque shaft may be attached to a motor or other drive mechanism via an end cap similar to the end cap 526 described above, but need not be. It should be appreciated that the torque shaft may be attached to a motor or other drive mechanism via an end cap in variations in which the torque shaft is connected to the cutter assembly via a counterbore, in variations in which the torque shaft is connected to the cutter assembly via an end cap, or in variations in which the torque shaft is connected to the cutter assembly via an end cap and a counterbore. In variations in which the torque shaft is attached to a motor or other drive mechanism via an end cap, the orientation of that end cap may be reversed from the orientation of the end cap 526 described above with respect to FIG. 5. That is, the distal portion of the end cap may be sized and configured to fit over the proximal end of the coiled shaft of the torque shaft, while the proximal portion of the end cap may be sized and configured to sit adjacent to the proximal end of the coiled shaft. In some variations, the end cap may be attached to the proximal end of the coiled shaft via soldering or the like, and the proximal end of the coiled shaft may have had accurate (concentric) centerless grinding of its proximal end, which may enable more precise attachment of the end cap. In variations in which the proximal end of the torque shaft is attached to a motor or other drive mechanism via an end cap, the proximal end of the end cap may be attached to a distal portion of the motor or other drive mechanism.

Coupling the torque shaft to the cutter and/or to the motor via end caps may improve the functioning of the atherectomy devices described herein and may increase the overall effectiveness of the cutter design. The end caps may be more easily manufactured with precision tolerances and greater consistency, which may allow for improved alignment of the torque shaft. The improved alignment of the torque shaft may improve performance by, for example, reducing wobble or vibration during rotation of the torque shaft and enabling proper balancing of a drive train. Coupling the torque shaft to the cutter and/or motor via end caps may also allow a higher strength coupling.

Handle

Figure 8A:
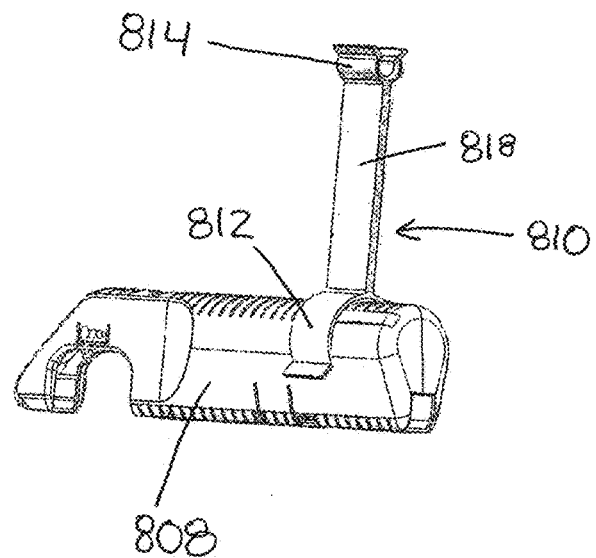
FIG. 8A depicts a perspective view of a representative handle and support clip as described here.
Figure 8B:
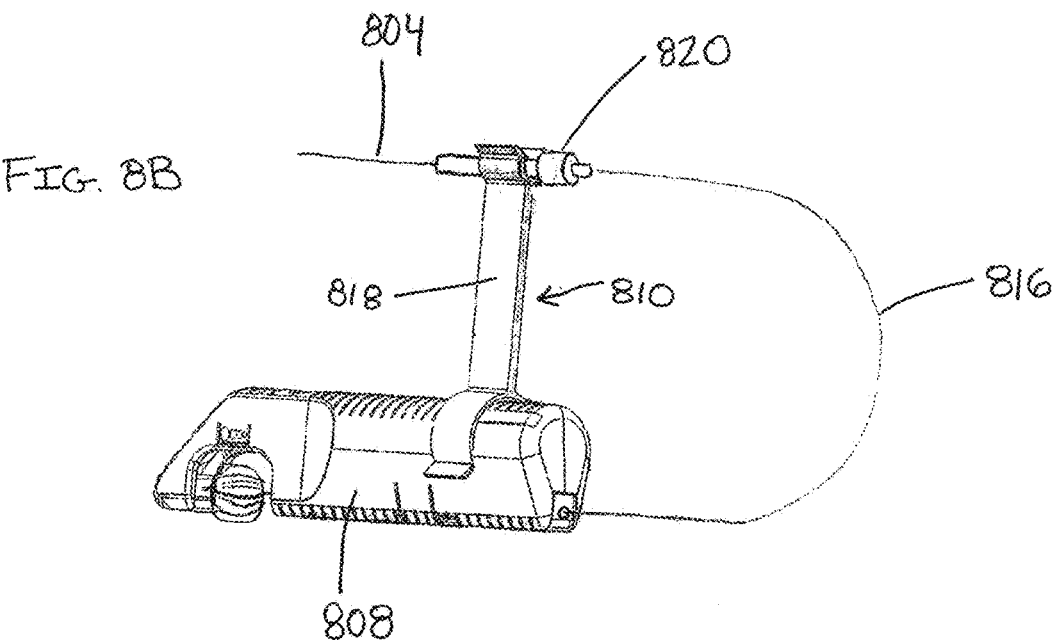
FIG. 8B depicts a perspective view of the handle and support clip of FIG. 8A with a guide wire forming a support loop as described here.

As mentioned above, the atherectomy apparatuses described herein may also include a handle, which may be coupled to the proximal (i.e., closest to the user) end of the catheter. FIGS. 8A and 8B depict a portion of a handle 808 of an atherectomy device, which may be attached to a catheter and/or a torque shaft of the device. As described above, the atherectomy system may include a guide wire 804 over which the atherectomy apparatus may be deployed, and in some variations, the atherectomy devices described herein may comprise a support clip 810 configured to releasably hold a portion of a guide wire 804 relative to a handle 808.

The support clip 810 may include a first clip portion 812 configured to connect the support clip 810 to the handle 808, a second clip portion 814 configured to connect the support clip 812 to the guide wire 804, and a central support arm 818 between the first clip portion 812 and the second clip portion 814. In some variations, the first clip portion 812 may comprise a flexible, semi-circular clip configured to removably snap onto or otherwise connect to the upper portion of the handle 808. It should be appreciated that the first clip portion 812 may attach to the handle 808 in any suitable way. For example, in other variations, the first clip portion 812 may comprise a widened portion configured to slide into a slot in the handle 808. In yet other variations, the first clip portion 812 may be permanently attached to the handle 808, or it may be integral to the handle 808. In some variations, the second clip portion 814 may comprise a smaller flexible, semi-circular shape configured to removably snap onto a guide wire holder 820, which may in turn be configured to receive the guide wire 804 therethrough.

The guide wire holder 820 may be located along the guide wire 804 at a distance from the proximal end of the handle 808. In some variations, the guide wire holder 820 may be fixed relative to the guide wire 408. When the guide wire holder 820 is snapped into the second clip portion 814 of the support clip 810, the guide wire 804 may form a support loop 816 having an arched shape, located between the proximal end of the handle 808 and the support clip 810. The guide wire 804 may thus have a first portion that extends from the handle 808 proximally; a second portion comprising the support loop 816; and a third portion that extends from the guide wire holder 820 distally. When the guide wire holder 820 is snapped into the support clip 810, the user may be able to move the handle 808 and catheter assembly while maintaining a distal guide wire position. Although the guide wire holder 820 in the variation of FIG. 8 is separate from the support clip 810 and may be reversibly attachable and removable from the support clip 810, it should be appreciated that in other variations the guide wire holder may be integral to the support clip 810, or it may be fixedly attached to the support clip 810. In such variations, the guide wire may be reversibly connectable and removable from the guide wire holder.

The support loop 816 may allow the atherectomy device to track freely over the guide wire 804 as a "rail," which may allow for automatic, single-operator control of the guide wire 804. Because the guide wire holder 820 is fixed relative to the guide wire 804, when a catheter of the atherectomy device is advanced distally along the guide wire 804, the length of the support loop 816 may increase. Conversely, when a catheter of the atherectomy device is retracted proximally along the guide wire 804, the length of the support loop 816 may decrease. In both cases, the position of the distal tip of the guide wire 804 within the vessel may remain constant as the catheter is moved. It may in some instances be desirable to have at least approximately 15 cm of guide wire distal to the distal end of the atherectomy device, which may provide distal traction to promote free tracking over the guide wire 804. It may also be desirable for the length of the support loop 816 to be at least the length of a region to be traversed during the procedure.

In order for the support loop 816 to allow the atherectomy device to track freely over the guide wire 804, it may be desirable for the support arm 818 of the support clip 810 to have a length such that the radius of curvature of the support loop 816 is sufficiently large. The support loop 816 may also impart dimensional stability to the guide wire 804 and may prevent rotation of the guide wire 804 during procedures, and may improve control and pushability of the guide wire 804 and catheter during procedures. In order to impart dimensional stability, it may be desirable for the support arm 818 of the support clip 810 to have a length such that the radius of curvature of the support loop 816 is between about 1 cm and about 10 cm. In other variations, the length of the support arm 818 may be such that the radius of curvature of the support loop 816 is between about 3 cm and about 8 cm. In other variations, the length of the support arm 818 may be such that the radius of curvature of the support loop 816 is between about 5 cm and about 6 cm. In other variations, the length of the support arm 818 may be such that the radius of curvature of the support loop 816 is about 5 cm. In other variations, the length of the support arm 818 may be such that the radius of curvature of the support loop 816 is greater than 10 cm.

Deflectable Atherectomy Systems and Apparatuses

Figure 13A:
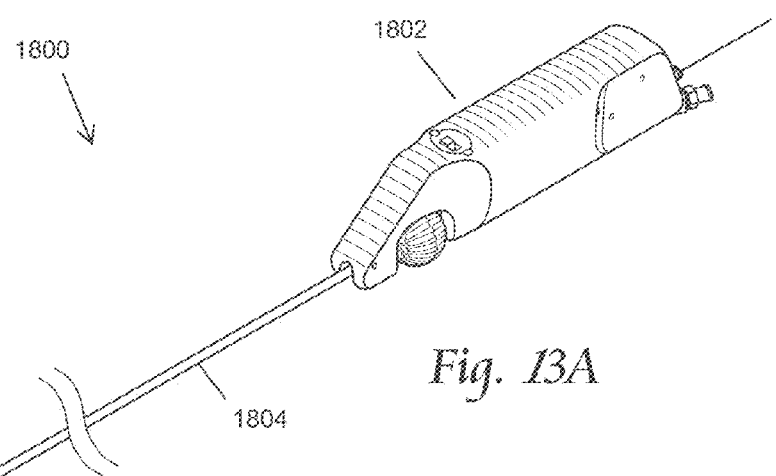
FIG. 13A depicts a perspective view of a variation of the atherectomy systems described here.
Figure 13B:
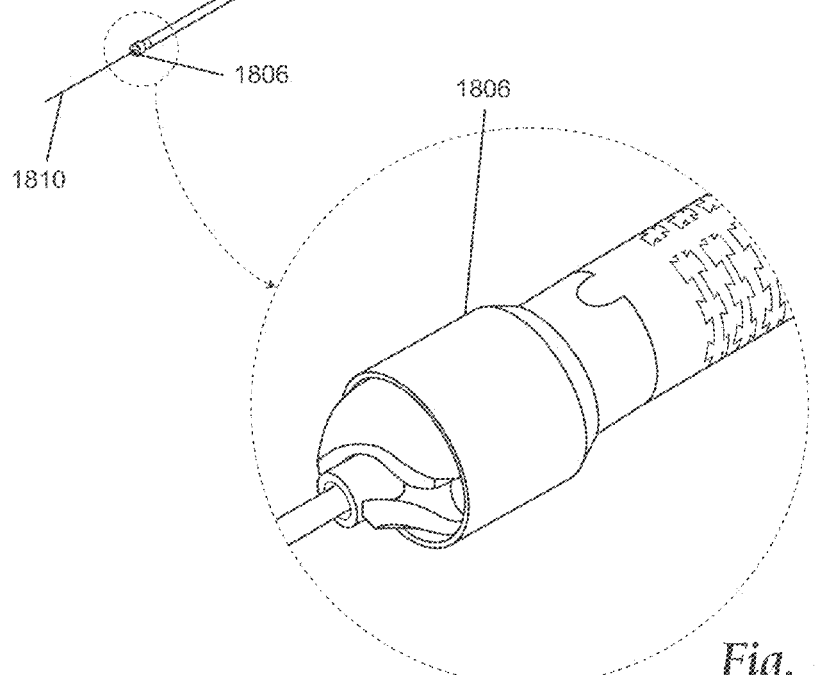
FIG. 13B is an enlarged perspective view of a distal portion of the atherectomy system shown in FIG. 13A.
Figure 13C:
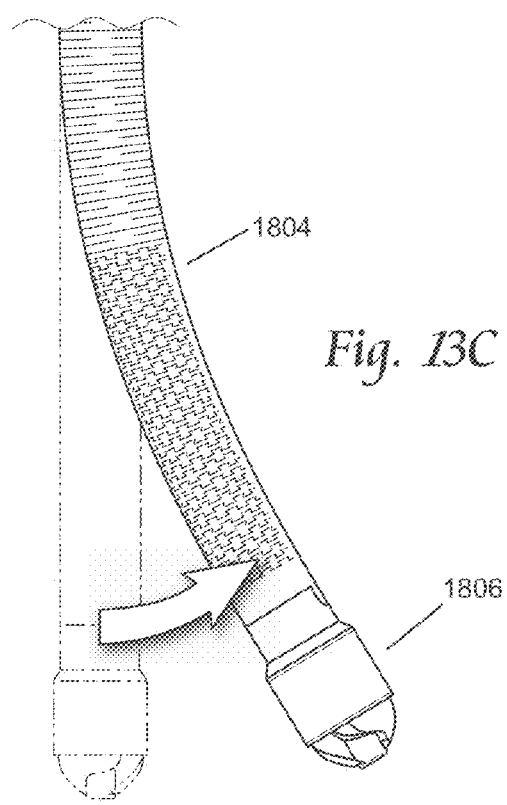
FIGS. 13C and 13D depict different manners in which the atherectomy system as shown in FIG. 13A may be manipulated.
Figure 13D:
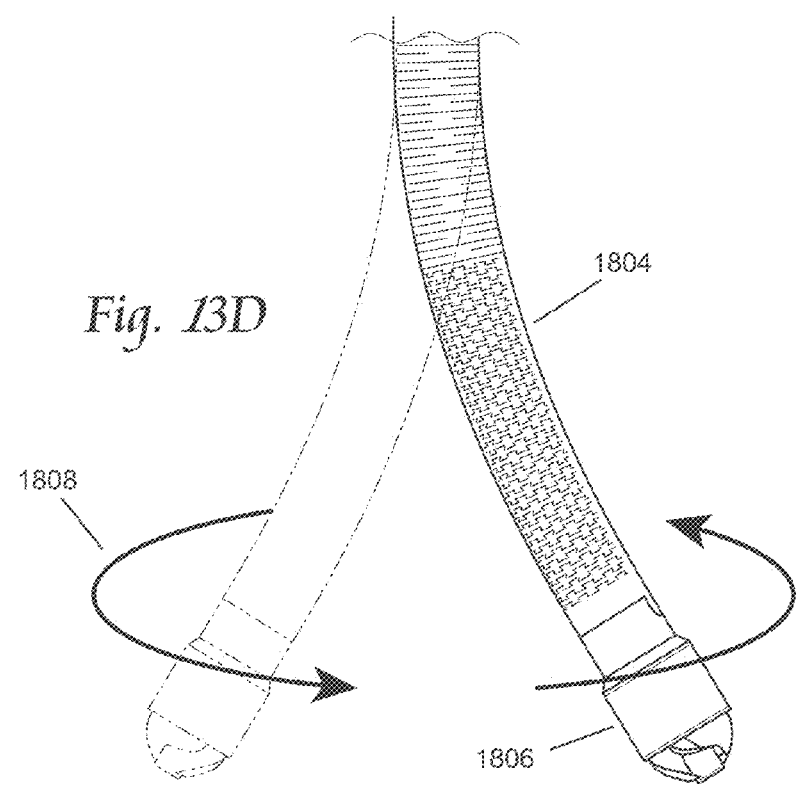

In some variations, the atherectomy systems described here may comprise an atherectomy apparatus configured to selectively dynamically deflect at its distal end (e.g., near a cutter assembly). For example, FIGS. 13A-13D show one variation of an atherectomy apparatus 1800 comprising a handle 1802, a catheter body 1804, and cutter assembly 1806. These elements may include any of the features previously described. As will be described in greater detail, the catheter body 1804 may be configured to dynamically deflect at its distal end (where the cutter assembly 1806 is carried) relative the central axis of the proximal catheter body 1804, as shown in FIG. 13C. This deflection may occur without axial advancement of the atherectomy apparatus. Additionally, the atherectomy apparatus 1800 may be configured to rotate the distal end of the apparatus while deflected about the central axis of the proximal catheter body 1804 to sweep the cutter assembly 1806 in an arc 1808 around the central axis, as shown in FIG. 13D. The ability of the atherectomy apparatus 1800 to sweep may allow for the cutter assembly to cut occlusive materials in a region larger than the outside diameter of the cutter assembly, as will be described in more detail below.

The atherectomy apparatus 1800 may be used in an atherectomy system including a guide wire 1810, and may be introduced into a blood vessel from an external percutaneous access site. The handle 1802 may be sized and configured to be securely held and manipulated by a caregiver outside an intravascular path in a manner previously described to advance the catheter along an intravascular. Image guidance (e.g., CT, radiographic, or guidance mechanisms, or combinations thereof), may be used to aid the caregiver's manipulation.

FIGS. 14A and 14B depict a variation of an atherectomy apparatus 1600 described here. As shown there, atherectomy apparatus 1600 may comprise a first catheter 1602, a second catheter 1604, and a cutter assembly 1605 attached to the first catheter 1602. The first catheter 1602 may be moveable relative to the second catheter 1604 to move a distal portion of the atherectomy apparatus 1600 between an undeflected configuration (as shown in FIG. 14A) and a deflected configuration (as shown in FIG. 14B). In the variation of atherectomy apparatus 1600 shown in FIGS. 14A and 14B, the first catheter 1602 may be moveable within the second catheter 1604, although it should be appreciated that in other variations the second catheter 1604 may be slidable within the first catheter 1602.

Generally, a distal portion 1606 of the second catheter 1604 may be shaped to take on a deflected position as shown in FIG. 14B. Specifically, the deflected distal portion 1606 may comprise a double curve having a first proximal curve 1608 and a second distal curve 1610. As shown there, the first curve 1608 may bend the distal portion 1606 away from the longitudinal axis 1612 of a proximal portion of the second catheter 1604, while the second curve 1610 may bend the distal portion 1606 in a direction toward the longitudinal axis 1612. The double-curve configuration of the distal portion 1606 may allow the second curve 1610 to contact or otherwise rest against a wall 1614 of a blood vessel 1616, as shown in FIG. 14B. Additionally, this may angle the cutter assembly 1605 toward an opposite vessel wall 1618 during cutting. In instances when the atherectomy apparatus 1600 is advanced over a guide wire 1620 as shown in FIG. 14B, the guide wire 1620 may contact the opposite vessel wall 1618 and may help to prevent the cutter assembly 1605 from directly contacting and/or damaging the vessel wall 1618. In some instances, the double-curve configuration of the distal portion 1606 may allow for advancement of the distal portion 1606 while deflected while minimizing the risk that the cutter assembly 1605 may catch on tissue and retroflex.

As mentioned above, the first catheter 1602 may be moved relative to the second catheter 1604 to move the atherectomy apparatus between deflected and undeflected configurations. Specifically, the first catheter 1602 may comprise a distal portion 1622 and a proximal portion (not shown), where the distal portion 1622 is more flexible than the proximal portion. Additionally, the distal portion 1622 of the first catheter 1602 may be more flexible than the distal portion 1606 of the second catheter 1604, while the proximal portion of the first catheter 1602 may be stiffer than the distal portion 1606 of the second catheter 1604. Accordingly, the first catheter 1602 may be advanced such that the flexible distal portion 1622 of the first catheter 1602 extends beyond the distal end of the second catheter 1604, which may the proximal portion of the first catheter 1602 within the distal portion 1606 of the second catheter 1604 (or around the distal portion 1606 of the second catheter 1604 in variations where the second catheter 1604 is positioned inside the first catheter 1602. Because the proximal portion of the first catheter 1602 is stiffer than the distal portion of the second catheter 1604, axial alignment of these catheter segments may cause the proximal portion of the first catheter 1602 to straighten out the curves of the distal portion of the second catheter 1604, thereby placing the atherectomy apparatus 1600 in an undeflected configuration, as shown in FIG. 14A. Because the flexible distal portion of the first catheter 1602 extends beyond the distal portion of the second catheter 1604 when in an undeflected configuration, it may be used to track the cutter assembly 1605 along a guide wire during navigation of the atherectomy apparatus 1600 through the vasculature. Additionally, the atherectomy apparatus 1600 may be advanced while cutting to cut along the path of the guide wire (which may be a straight path in some instances), as described in more detail below. The atherectomy apparatus 1600 may then be withdrawn and deflected to cut a larger path through occlusive material (not shown), such as described below.

To move the atherectomy apparatus to a deflected configuration, the first catheter 1602 may be withdrawn to place the flexible distal portion 1622 of the first catheter 1602 in axial alignment with the distal portion 1606 of the second catheter 1604. Because the distal portion 1606 of the second catheter 1604 is stiffer than the distal portion 1622 of the first catheter 1602, the second catheter 1604 may cause the flexible distal portion 1622 of the first catheter 1602 to take on the dual-curve configuration described above with respect to FIG. 14B.

Mechanical Removal of Occlusive Materials

Figure 15:
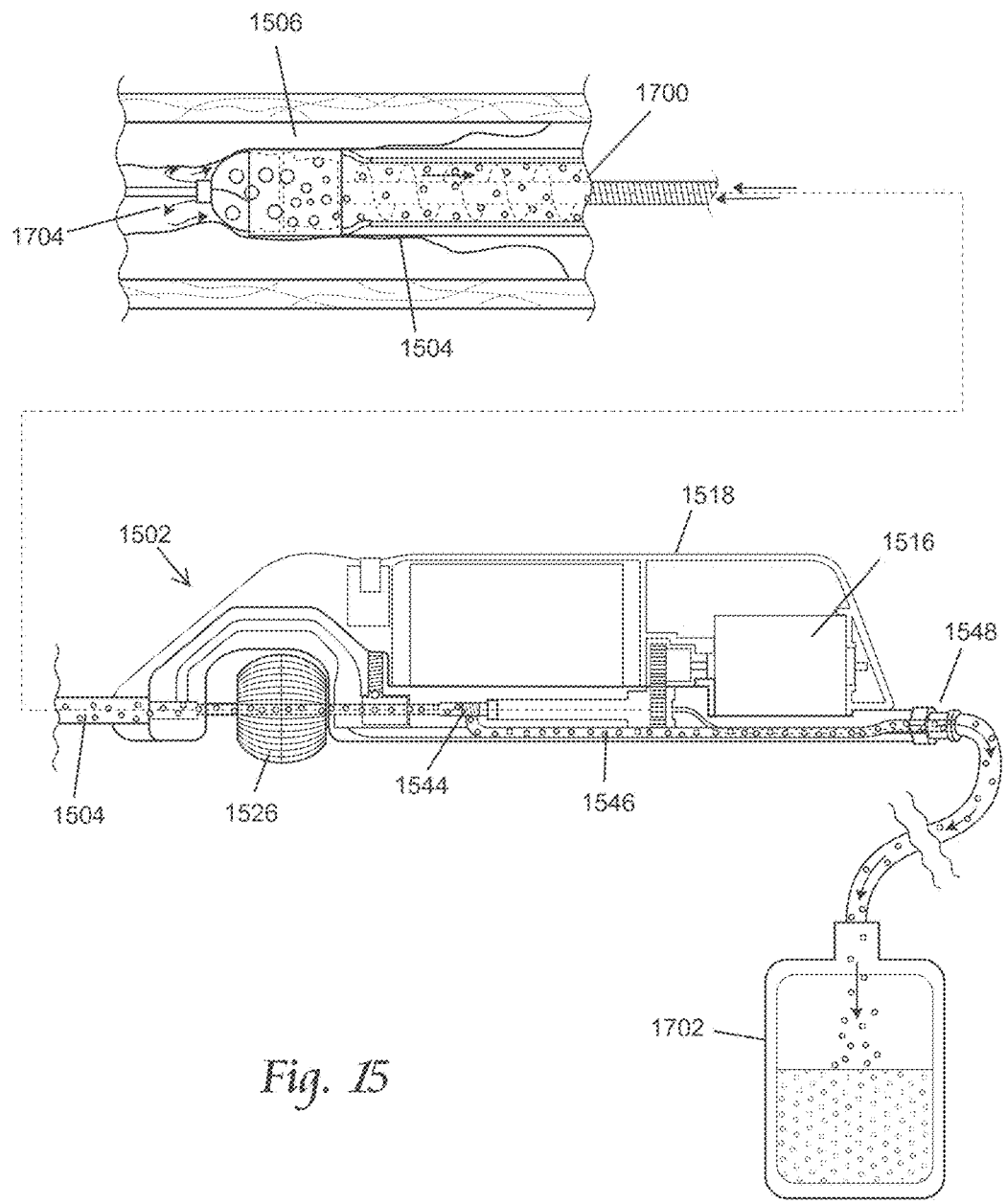
FIG. 15 depicts a cross-sectional side view of a variation of the catheter assemblies described here.

As mentioned above, in some variations of the atherectomy apparatuses described here, the atherectomy apparatus includes an internal conveying member. For example, the atherectomy apparatus may comprise an internal conveyor. In variations that include an internal conveying member, the internal conveying member may comprises a wire helically wound about the torque shaft in a direction common with the helical cutting surfaces of the cutter assembly. When a cutter assembly cuts and captures occlusive material (e.g., when the helical flutes of a distal and/or proximal cutter conveys cut and captured occlusive materials to the conveying member), the conveying member may rotate in common with a torque shaft to convey the cut and captures occlusive materials it receives from the cutter assembly further back (proximally) along the catheter body into the handle. For example, FIG. 15 shows a variation of an atherectomy apparatus 1500 conveying and transferring occlusive material 1700 proximally through the apparatus.

The occlusive materials carried back by the conveying element into the handle may be transferred into a discharge passage within the handle. A transfer propeller communicating with the discharge passage may be coupled to the torque shaft to rotate in common with the torque shaft, and may act to pump the cut, captured, and conveyed occlusive materials into the discharge passage. The discharge passage may include an external coupler (e.g., a leur connector) to couple the discharge passage to an external waste container. The cut and captured occlusive materials may be conveyed into the waste receptacle, and may be done so without need for vacuum aspiration. For example, as shown in FIG. 15, atherectomy apparatus 1500 may comprise a transfer propeller 1544, a discharge passage 1546, and an external coupler 1548, which may be connected to an external waste container 1702 as just described.

In some instances, it may be desirable to convey saline or another biocompatible fluid down the catheter body for mixing with occlusive material within the cutter assembly. Mixing the fluid with the occlusive materials may form a slurry, which may reduce the viscosity of the materials cut, captured, and conveyed from the vessel by the atherectomy apparatus. This may reduce the load imposed on the cutter assembly and facilitate the transfer of materials into the waste receptacle. As shown in FIG. 15, the atherectomy apparatus 1500 may convey a fluid 1704 from the distal end of the device. In some variations, the fluid 1704 may be conveyed through an internal/guide wire lumen within the torque shaft 1522.

We claim:

1. A device for removing occlusive material from a vessel, comprising:
   a catheter; and
   a cutter assembly coupled to a distal end of the catheter;
   wherein the cutter assembly comprises a cutter comprising helical flutes, wherein the cutter comprises a proximal cutter and a distal cutter;
   wherein the cutter assembly further comprises a guide wire lumen, and a port, wherein the port comprises an opening extending from the guide wire lumen to an outside surface of the cutters;
   wherein the port is an opening port to exit material entered into the guide wire lumen after entering to be recaptured by the cutter assembly; and
   wherein the proximal cutter comprises a stem configured to fit within a central lumen of the distal cutter, and wherein the port is located on the stem of the proximal cutter.

2. The device of claim 1, wherein the port has a cross-sectional area of less than 50% of a cross-sectional area of a stem.

3. The device of claim 1, wherein a first portion of the stem of the proximal cutter is covered by the distal cutter, and a second portion of the stem of the proximal cutter is exposed by the distal cutter, and wherein the port is exposed by the distal cutter.

4. The device of claim 1, wherein a first portion of the stem of the proximal cutter is covered by the distal cutter, and a second portion of the stem of the proximal cutter is exposed by the distal cutter, and wherein the port is covered by the distal cutter, further comprising a second port in the distal cutter, wherein the port on the stem of the proximal cutter and the second port form a contiguous opening from the central lumen of the cutter assembly through the proximal and distal cutters.

5. The device of claim 1, wherein the port is angled proximally from the central lumen to the outside surface of the cutter.

6. The device of claim 1, wherein a cross-sectional area of the port increases from the central lumen to the outside surface of the cutter.

7. The device of claim 1, wherein the cutter assembly comprises a cutter housing and wherein the proximal cutter is at least partially housed within the housing.

8. The device of claim 7, wherein the cutter assembly provides a two-stage cutting action, wherein in operation the distal cutter cuts occlusive material and conveys the material to the proximal cutter and the proximal cutter cuts or macerates the occlusive material into smaller particles.

\* \* \* \* \*